US010662478B2

(12) United States Patent
Suh et al.

(10) Patent No.: US 10,662,478 B2
(45) Date of Patent: May 26, 2020

(54) SERINE PROTEASES AS BIOMARKERS FOR OVARIAN CANCER

(71) Applicant: Hackensack University Medical Center, Hackensack, NJ (US)

(72) Inventors: K. Stephen Suh, Hackensack, NJ (US); Ayala Tamir, Hackensack, NJ (US); Andrew L. Pecora, Wycoff, NJ (US)

(73) Assignee: Hackensack University Medical Center, Hackensack, NJ (US)

( * ) Notice: Subject to any disclaimer, the term of this patent is extended or adjusted under 35 U.S.C. 154(b) by 287 days.

(21) Appl. No.: 14/838,945

(22) Filed: Aug. 28, 2015

(65) Prior Publication Data

US 2016/0097102 A1    Apr. 7, 2016

Related U.S. Application Data

(60) Provisional application No. 62/043,290, filed on Aug. 28, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01); *G01N 2333/96433* (2013.01); *G01N 2800/52* (2013.01)

(58) Field of Classification Search
None
See application file for complete search history.

(56) References Cited

U.S. PATENT DOCUMENTS

2006/0134120 A1    6/2006  Diamandis

OTHER PUBLICATIONS

Tannir et al; Journal of Ovarian Research 2014, vol. 7, pp. 1-15.*
Verghese et al., "Prostasin regulates epithelial monolayer function: cell-specific Gpld1-mediated secretion and functional role for GPI anchor," American Journal of Physiology—Cell Physiology vol. 291, No. 6, Dec. 1, 2006, pp. C1258-C1270.
Vuagniaux et al., "Activation of the Amiloride-Sensitive Epithelial Sodium Channel by the Serine Protease mCAP1 Expressed in a Mouse Cortical Collecting Duct Cell Line," Journal of the American Society of Nephrology 11, May 1, 2000, pp. 828-834.
Vuagniaux et al., "Synergistic Activation of ENaC by Three Membrane-bound Channel-activating Serine Proteases (mCAP1, mCAP2, and mCAP3) and Serum- and Glucocorticoid-regulated Kinase (Sgk1) in Xenopus Oocytes," Journal of General Physiology vol. 120 No. 2, Aug. 2002, pp. 191-201.
White et al., "KLK6 and KLK13 predict tumor recurrence in epithelial ovarian carcinoma," British Journal of Cancer (2009) 101, published online: Aug. 25, 2009, pp. 1107-1113.
Yurkovetsky et al., "Development of a Multimarker Assay for Early Detection of Ovarian Cancer," Journal of Clinical Oncology, vol. 28 No. 13, May 1, 2010, pp. 2159-2166.
Zhang et al., "The Road from Discovery to Clinical Diagnostics: Lessons Learned from the First FDA-Cleared In Vitro Diagnostic Multivariate Index Assay of Proteomic Biomarkers," Cancer Epidemiol Biomarkers Prev., Published Online: Oct. 20, 2010, pp. 2995-2999.
Karlan et al., "Randomized, Double-Blind, Placebo-Controlled Phase II Study of AMG 386 Combined With Weekly Paclitaxel in Patients With Recurrent Ovarian Cancer," Journal of Clinical Oncology, vol. 30, No. 4, Feb. 1, 2012, pp. 362-370.
Sarojini S., et al., "Early detection biomarkers for ovarian cancer", Journal of Oncology, 2012, vol. 2012 pp. 1-15.
"New FIGO Ovarian Cancer Staging guidelines", Society of Gynecologic Oncology, 2014, pp. 1-2, www.sgo./wp-content/uploads/2012/09/FIGO-Ovarian-Cancer-Staging_1.10.14pdf.
Tamir A., et al., "Kallikrein family proteases KLK6 and KLK7 are potential early detection and diagnostic biomarkers for serous and papillary serous ovarian cancer subtypes", Journal of Ovarian Research, 2014, vol. 7, pp. 1-15.
Aghajanian et al., "Oceans:A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer," Journal of Clinical Oncology, Apr. 23, 2012, 7 pgs.
Altekruse F. et al., "SEER Cancer Statistics Review, 1975-2007," Bethesda, MD: National Cancer Institute; 2010, 22 pgs.
Biagi et al., "A phase II study of sunitinib in patients with recurrent epithelial ovarian and primary peritoneal carcinoma: an NCIC Clinical Trials Group Study," Annals of Oncology vol. 22, Issue 2, pp. 335-340, First published Online: Aug. 12, 2010.
Blaber et al., "The Autolytic Regulation of Human Kallikrein-Related Peptidase 6," Biochemistry, Apr. 7, 2007, 46 (17), pp. 5209-5217.
Burger et al., "Incorporation of Bevacizumab in the Primary Treatment of Ovarian Cancer," The New England Journal of Medicine 365;26, Dec. 29, 2011, pp. 2473-2483.
Chen et al., "Invasion patterns in stage I endometrioid and mucinous ovarian carcinomas: a clinicopathologic analysis emphasizing favorable outcomes in carcinomas without destructive stromal invasion and the occasional malignant course of carcinomas with limited destructive stromal invasion," Modern Pathology (2005) 18, Published Online: Jan. 14, 2005, pp. 903-911.

(Continued)

*Primary Examiner* — Jehanne S Sitton
(74) *Attorney, Agent, or Firm* — McCarter & English, LLP; Beverly W. Lubit

(57) ABSTRACT

The described invention provides methods for detecting, diagnosing and treating low-grade ovarian cancer and stage I ovarian cancer by comparing results from serum and ovarian tissue samples with normal controls. An increased level of expression of serine protease, wherein the serine protease is at least 2 selected from the group consisting of kallikrein 6 (KLK6), kallikrein 7 (KLK7), and PRSS8, expressed by subject samples compared to the level of expression of serine protease expressed by normal control samples is indicative of possible early stage ovarian cancer in the subject. Once early stage (I/II) ovarian cancer is diagnosed, the subject is treated with a treatment regimen effective to treat the early stage (I/II) ovarian cancer.

9 Claims, 15 Drawing Sheets

Specification includes a Sequence Listing.

(56) References Cited

OTHER PUBLICATIONS

Costa et al., "Prostasin, A Potential Tumor Marker in Ovarian Cancer—A Pilot Study," Clinical Science, Clinics. 2009; 64(7): pp. 641-644.
Dong et al., "Kallikrein-Related Peptidase 7 Promotes Multicellular Aggregation via the α5β1 Integrin Pathway and Paclitaxel Chemoresistance in Serous Epithelial Ovarian Carcinoma," The Journal of Cancer Research 70(7); Apr. 1, 2010, pp. 2624-2633.
Eissa et al., "Human tissue kallikreins as promiscuous modulators of homeostatic skin barrier functions," Biol. Chem., vol. 389, Jun. 2008, pp. 669-680.
Emami et al., "New insights into the functional mechanisms and clinical applications of the kallikrein-related peptidase family," Molecular Oncology, vol. 1, Issue 3, Dec. 2007, pp. 269-287.
Fong et al., "Poly(ADP)-Ribose Polymerase Inhibition: Frequent Durable Responses in BRCA Carrier Ovarian Cancer Correlating With Platinum-Free Interval," The Journal of Clinical Oncology, vol. 28, No. 15, May 20, 2010, pp. 2512-2519.
Gubbels et al., "The detection, treatment, and biology of epithelial ovarian cancer," Journal of Ovarian Research 2010, 3:8, 11 pgs.
Hanahan et al., "Hallmarks of Cancer: The Next Generation," Cell, vol. 144, Issue 5, Mar. 4, 2011, pp. 646-674.
Itamochi, "Targeted therapies in epithelial ovarian cancer: Molecular mechanisms of action," World J Biol Chem., Jul. 26, 2010; 1(7): 209-220.
Jelovac et al., "Recent progress in the diagnosis and treatment of ovarian cancer," CA: A Cancer Journal for Clinicians vol. 61, Issue 3, May/Jun. 2011, pp. 183-203.
Karp et al., "An Evidence Ontology for Use in Pathway/Genome Databases," Pac. Symp. Biocomput. 2004:190-201, 12 pgs.
Kim et al., "Therapeutic strategies in epithelial ovarian cancer," Journal of Experimental & Clinical Cancer Research 2012, 31:14, 8 pgs.
Kim et al., "High-grade serous ovarian cancer arises from fallopian tube in a mouse model," Proceedings of the National Academy of Sciences of the United States of America, vol. 109 No. 10, Mar. 6, 2012, pp. 3921-3926.
Kyriakopoulou et al., "Prognostic value of quantitatively assessed KLK7 expression in ovarian cancer," Clinical Biochemistry, vol. 36, Issue 2, Mar. 2003, pp. 135-143.
Ledermann et al., "Randomized Phase II Placebo-Controlled Trial of Maintenance Therapy Using the Oral Triple Angiokinase Inhibitor BIBF 1120 After Chemotherapy for Relapsed Ovarian Cancer," Journal of Clinical Oncology, vol. 29, No. 28, Oct. 1, 2011, pp. 3798-3804.
Levanon et al., "New Insights Into the Pathogenesis of Serous Ovarian Cancer and Its Clinical Impact," Journal of Clinical Oncology, vol. 26 No. 32, Nov. 10, 2008, pp. 5284-5293.
Lu et al., "Selection of Potential Markers for Epithelial Ovarian Cancer with Gene Expression Arrays and Recursive Descent Partition Analysis," Clinical Cancer Research, vol. 10, May 15, 2004, pp. 3291-3300.
Matei et al., "Activity of Sorafenib in Recurrent Ovarian Cancer and Primary Peritoneal Carcinomatosis: A Gynecologic Oncology Group Trial," Journal of Clinical Oncology, vol. 29, No. 1, Jan. 1, 2011, pp. 69-75.
Matulonis et al., "Cediranib, an Oral Inhibitor of Vascular Endothelial Growth Factor Receptor Kinases, Is an Active Drug in Recurrent Epithelial Ovarian, Fallopian Tube, and Peritoneal Cancer," Journal of Clinical Oncology, vol. 27, No. 33, Nov. 20, 2009, pp. 5601-5606.
McConechy et al., "Ovarian and endometrial endometrioid carcinomas have distinct CTNNB1 and PTEN mutation profiles," Modern Pathology (2014) 27, published online; Jun. 14, 2013, pp. 128-134.
McIntosh et al., "Validation and Characterization of Human Kallikrein 11 as a Serum Marker for Diagnosis of Ovarian Carcinoma," Clin Cancer Res 2007;13(15), Aug. 1, 2007, pp. 4422-4428.
Mitsui et al., "A novel serine protease highly expressed in the pancreas is expressed in various kinds of cancer cells," The FEBS Journal, vol. 272, Issue 19, Oct. 2005, pp. 4911-4923.
Mok et al., "Prostasin, a Potential Serum Marker for Ovarian Cancer: Identification Through Microarray Technology," Journal of the National Cancer Institute, vol. 93, Issue 19, Oct. 3, 2001, pp. 1458-1464.
Nagahara et al., "Clinicopathologic and Biological Significance of Kallikrein 6 Overexpression in Human Gastric Cancer," Clin. Cancer Res. 2005;11(19) Oct. 1, 2005, pp. 6800-6806.
Nathalie et al., "High kallikrein-related peptidase 6 in non-small cell lung cancer cells: an indicator of tumour proliferation and poor prognosis," Journal of Cellular and Molecular Medicine, vol. 13, Issue 9b, Sep. 2009, pp. 4014-4022.
Perren et al., "A Phase 3 Trial of Bevacizumab in Ovarian Cancer," The New England Journal of Medicine 2011; 365, Dec. 29, 2011, pp. 2484-2496.
Planès et al., "ENaC—mediated alveolar fluid clearance and lung fluid balance depend on the channel—activating protease 1," EMBO Molecular Medicine (2009) 2, Published online: Sep. 11, 2009, pp. 26-37.
Ramirez et al.,"The Role of Surgery in the Management of Epithelial Ovarian Cancer," Cancer Control, Jan. 2011;18 (1), pp. 22-30.
Rein et al., "Potential Markers for Detection and Monitoring of Ovarian Cancer," Journal of Oncology, vol. 2011 (2011), Article ID 475983, 17 pages.
Schilder et al., "Phase II Study of Gefitinib in Patients with Relapsed or Persistent Ovarian or Primary Peritoneal Carcinoma and Evaluation of Epidermal Growth Factor Receptor Mutations and Immunohistochemical Expression: A Gynecologic Oncology Group Study," Clin. Cancer Res. 2005;11(15) Aug. 1, 2005, pp. 5539-5548.
Shan et al., "Unfavorable Prognostic Value of Human Kallikrein 7 Quantified by ELISA in Ovarian Cancer Cytosols," Clinical Chemistry 52:10, Oct. 2006, pp. 1879-1886.
Shaw et al., "Distribution of 15 Human Kallikreins in Tissues and Biological Fluids," Clinical Chemistry 53:8, Aug. 2007, pp. 1423-1432.
Sotiropoulou et al., "Functional Roles of Human Kallikrein-related Peptidases," Journal of Biological Chemistry 284 (48), Nov. 27, 2009, 11 pgs.
Sugiyama et al., "Clinical characteristics of clear cell carcinoma of the ovary," Cancer vol. 88, Issue 11, Jun. 1, 2000 pp. pp. 2584-2589.
Tan et al., "Ovarian clear cell adenocarcinoma: a continuing enigma," Journal of Clinical Pathology 2007;60, Published Online: Oct. 3, 2006, pp. 355-360.
Teramukai et al., "PIEPOC: A New Prognostic Index for Advanced Epithelial Ovarian Cancer—Japan Multinational Trial Organization OC01-01," Journal of Clinical Oncology, vol. 25, No. 22, Aug. 1, 2007, pp. 3302-3306.
Tong et al., "Expression of PAX2 in papillary serous carcinoma of the ovary: immunohistochemical evidence of fallopian tube or secondary Müllerian system origin?," Modern Pathology (2007) 20, published online: May 25, 2007, pp. 856-863.
Trimbos et al., "International Collaborative Ovarian Neoplasm Trial 1 and Adjuvant ChemoTherapy in Ovarian Neoplasm Trial: Two Parallel Randomized Phase III Trials of Adjuvant Chemotherapy in Patients With Early-Stage Ovarian Carcinoma," Journal of the National Cancer Institute, vol. 95, No. 2, Jan. 15, 2003, pp. 105-112.
Anderson, et al; Assessing Lead Time of Selected Ovarian Cancer Biomarkers: A Nested Case—Control Study, Journal of the National Cancer Institute, vol. 102, Issue 1, Jan. 6, 2010, pp. 26-38.
Chen, et al; Loss of prostasin (PRSS8) in human bladder transitional cell carcinoma cell lines is associated with epithelial-mesenchymal transition (EMT), BMC Cancer 2009, 9:377, 12 pgs.
Nolen, et al; Serum biomarker panels for the discrimination of benign from malignant cases in patients with an adnexal mass, Gynecol Oncol. Jun. 2010 ; 117(3): 440-445.
Oikonomopoulou, et al, Functional proteomics of kallikrein-related peptidases in ovarian cancer ascites fluid*, Biol. Chem., vol. 391, pp. 381-390, Apr. 2010.
Rouleau, et al, PARP inhibition: PARP1 and beyond, Nat Rev Cancer. Apr. 2010 ; 10(4): 293-301.

(56) References Cited

OTHER PUBLICATIONS

Selzer-Plon, et al, Expression of prostasin and its inhibitors during colorectal cancer carcinogenesis, BMC Cancer 2009, 9:201-210.
Sotiropoulou, et al; Kallikrein-related peptidases: bridges between immune functions and extracellular matrix degradation; Biol. Chem., vol. 391, pp. 321-331, Apr. 2010.
Vang, et al; Ovarian Low-Grade and High-Grade Serous Carcinoma: Pathogenesis, Clinicopathologic and Molecular Biologic Features, and Diagnostic Problems, Adv Anat Pathol. Sep. 2009 ; 16(5): 267-282.
Yu, et al; Prostasin is a novel human serine proteinase from seminal fluid. Purification, tissue distribution, and localization in prostate gland; J Biol Chem vol. 269, No. 29, 18843-18848, 1994.

\* cited by examiner

\* P<0.01
\*\* P<0.05

SEQUENCE LISTING

<160> NUMBER OF SEQ ID NOS: 3

<210> SEQ ID NO 1

```
<211> LENGTH: 21
<212> TYPE: DNA
<213> ORGANISM: Artificial Sequence
<220> FEATURE:
<223> OTHER INFORMATION: Digoxigenin-labeled probe

<400> SEQUENCE: 1
gaccaagtcc tcactcatca c                                              21

<210> SEQ ID NO 2
<211> LENGTH: 22
<212> TYPE: DNA
<213> ORGANISM: Artificial Sequence
<220> FEATURE:
<223> OTHER INFORMATION: Digoxigenin-labeled probe

<400> SEQUENCE: 2
aaagtacaca gaaggaagga ga                                             22

<210> SEQ ID NO 3
<211> LENGTH: 22
<212> TYPE: DNA
<213> ORGANISM: Artificial Sequence
<220> FEATURE:
<223> OTHER INFORMATION: Digoxigenin-labeled probe

<400> SEQUENCE: 3
gcagtaaaac tcctgactct ca                                             22
```

SERINE PROTEASES AS BIOMARKERS FOR OVARIAN CANCER

CROSS-REFERENCE TO RELATED APPLICATION

This application claims the benefit of priority to U.S. Provisional Application No. 62/043,290 (filed Aug. 28, 2014), entitled "Kallikrein Family Proteases KLK6 and KLK7 as Biomarkers for Ovarian Cancer," the content of which is incorporated by reference herein in its entirety.

FIELD OF THE INVENTION

The described invention generally relates to ovarian cancer.

BACKGROUND

Ovarian Cancer

Ovarian cancer ranks as the fifth most common cancer in women and has the highest mortality rate among gynecologic malignancies (Suh K S, Park S W, Castro A, Patel H, Blake P, Liang M, et al. Ovarian cancer biomarkers for molecular biosensors and translational medicine. Expert Rev Mol Diagn 2010; 10:1069-83; Landen C N Jr, Birrer M J, Sood A K. Early events in the pathogenesis of epithelial ovarian cancer. J Clin Oncol 2008; 26:995-1005). Although the 5-year survival rate of ovarian cancer is around 90% when detected in early stages (I/II), nearly 80% of the new cases are diagnosed in advanced stages (III/IV) because of the asymptomatic nature of the disease at stage I and early stage II. Unfortunately, the 5-year survival rate of advanced ovarian cancer is as low as 11% (Altekruse S F, Kosary C L, Krapcho M, Neyman N, Aminou R, Waldron W, et al. *SEER Cancer Statistics Review,* 1975-2007, National Cancer Institute. Bethesda, Md.). Therefore, there is a need to find reliable biomarkers for early detection of ovarian cancer.

Types of Ovarian Cancer

Ovarian cancer is not a single disease but consists of more than 30 types and subtypes of malignancies, each with its own histopathologic appearance and biologic behavior. Generally, ovarian cancers are grouped into 3 major categories: (1) epithelial tumors (tumors arising from cells that line or cover the ovaries); (2) germ cell tumors (tumors that originate from cells that are destined to form eggs within the ovaries; and (3) sex cord-stromal cell tumors (tumors that begin in connective cells that hold the ovaries together and produce female hormones). The most common ovarian cancers are epithelial tumors, which account for about 90% of all ovarian cancers. Ovarian epithelial tumors are divided into subtypes which include serous, papillary serous, endometrioid, mucinous and clear cell tumors.

Common Epithelial Tumors

Serous

The serous subtype of ovarian carcinoma accounts for approximately 60-80% of ovarian cancer cases and exhibits the most aggressive histology (Levanon K. et al., J. Clinical Oncology, Nov. 10, 2008 Vol. 26 No. 32 5284-5293). Fewer than 25% of serous ovarian cancer cases are detected at an early stage (stages I and II), which reflects grimly on survival figures (Seidman J. D. et al., Int. J. Gynecol. Pathol. 23:41-44, 2004). High-grade serous carcinoma involves the surface of the ovary, often bilaterally, and the peritoneal membranes, with rapid onset of carcinomatosis, a fact that restricts the surgical options to debulking only (Levanon K. et al., J. Clinical Oncology, Nov. 10, 2008 Vol. 26 No. 32 5284-5293). Despite the introduction of taxanes to therapeutic protocols and the prolonged survival with intraperitoneal chemotherapy administration, there has been little progress in improving cure rates, a parameter that is still solely dependent on the disease stage at the time of presentation (Levanon K. et al., J. Clinical Oncology, Nov. 10, 2008 Vol. 26 No. 32 5284-5293).

Papillary Serous

Papillary serous carcinoma of the ovary is one of the most common and lethal malignant tumors (Tong G-X et al., Modern Pathology (2007) 20, 856-863). Papillary serous histology accounts for 75% of ovarian cancers and its histological pattern simulates the lining of the fallopian tube (Jelovac D. and Armstrong D. K., CA: A Cancer Journal for Clinicians, Vol. 61, Issue 3, pp. 183-203, May/June 2011). Most cases of papillary serous ovarian cancer are diagnosed at advanced stages, when the tumors have already metastasized (Kim J. et al., PNAS, Mar. 6, 2012, Vol. 109, No. 10, pp. 3921-3926). Despite the steady improvement of surgery and chemotherapy, greater than 90% of women with advanced ovarian cancers die after relapse (Bukowski R. M. et al. (2007) Semin. Oncol. 34(Suppl 2):S1-S15). Early detection of these high-grade serous carcinomas is thus key to reducing ovarian cancer deaths (Bast R. C. Jr. et al. (2009) Nat. Rev. Cancer 9:415-428).

Endometrioid

Ovarian endometrioid carcinomas account for only 10% of ovarian carcinomas (McConechy M. K. et al., Modern Pathology (2007) 27, 128-134). The majority of ovarian endometrioid carcinomas are low-grade carcinomas with good prognosis (Chen S. et al., Modern Pathology (2005) 18:903-911).

Mucinous

The mucinous cell type accounts for approximately 10% of all primary epithelial ovarian carcinomas (Chan J. K. et al., Gynecol. Oncol. 2008; 109:370-376). Most mucinous epithelial ovarian carcinomas are diagnosed early (International Federation of Gynecology and Obstetrics (FIGO) stages I-IIA) and confined to one ovary. In stage I mucinous epithelial ovarian carcinomas, the 5-year disease-free survival rate is about 90%, which is slightly better than the 76% observed for patients with serous epithelial ovarian carcinomas (Vergote I. et al., Lancet 2001; 357:176-182). Less frequently, primary mucinous epithelial ovarian carcinoma is associated with peritoneal carcinomatosis and/or extraperitoneal metastases (FIGO stages IIB-IV). Unlike FIGO stage I tumors, advanced mucinous epithelial ovarian carcinomas reportedly have poorer prognoses than serous epithelial ovarian carcinomas (Omura G. A. et al., J. Clin. Oncol. 1991; 9:1138-1150; Teramukai S. et al., J. Clin. Oncol. 2007; 25:3302-3306).

Clear Cell

Ovarian clear cell adenocarcinomas account for <5% of all ovarian malignancies and 3.7-12.1% of all epithelial ovarian carcinomas (Tan D. S. P. and Kaye S., J. Clin. Pathol. April 2007; 60(4): 355-360). Compared to other epithelial ovarian cancer (EOC) subtypes, when at an advanced stage, they are associated with a poorer prognosis and are relatively resistant to conventional platinum-based chemotherapy (Sugiyama T. et al., Cancer. 2000 Jun. 1; 88(11):2584-9). By contrast, early-stage clear cell ovarian cancer carries a relatively good prognosis (Tan D. S. P. and Kaye S., J. Clin. Pathol. April 2007; 60(4): 355-360). Hence, early detection is the key to improve prognosis and reduce deaths associated with this type of ovarian cancer.

Ovarian Cancer Staging

The process used to determine whether ovarian cancer has spread within the ovaries or to other parts of the body (i.e., metastasized) is called staging. It is important to determine the stage of ovarian cancer because the stage will determine the type of treatment plan selected to combat the disease. The results of tests used to diagnose ovarian cancer are often also used to stage the disease. Such tests include ultrasound, computerized tomography (CT) scan, positron emission tomography (PET) scan, magnetic resonance imaging (MRI), X-ray and biopsy. Ovarian cancer staging guidelines have been developed by the International Federation of Gynecologists and Obstetricians (FIGO). The FIGO staging system for ovarian cancer is shown in Table 1.

TABLE 1

FIGO Ovarian Cancer Staging

| Stage | Area of Involvement |
| --- | --- |
| IA | Tumor limited to 1 ovary, capsule intact, no tumor on surface, negative washings |
| IB | Tumor involves both ovaries; otherwise like IA |
| IC1 | Surgical spill |
| IC2 | Capsule rupture before surgery or tumor on ovarian surface |
| IC3 | Malignant cells in the ascites or peritoneal washings |
| IIA | Extension and/or implant on uterus and/or Fallopian tubes |
| IIB | Extension to other pelvic intraperitoneal tissues |
| IIIA1 | Positive retroperitoneal lymph nodes only<br>IIIA1(i) - Metastasis ≤10 mm<br>IIIA1(ii) - Metastasis >10 mm |
| IIIA2 | Microscopic, extrapelvic (above the brim) peritoneal involvement ± positive retroperitoneal lymph nodes |
| IIIB | Macroscopic, extrapelvic, peritoneal metastasis ≤2 cm ± positive retroperitoneal lymph nodes; includes extension to capsule of liver/spleen |
| IIIC | Macroscopic, extrapelvic, peritoneal metastasis >2 cm ± positive retroperitoneal lymph nodes; includes extension to capsule of liver/spleen |
| IVA | Pleural effusion with positive cytology |
| IVB | Hepatic and/or splenic parenchymal metastasis, metastasis to extra-abdominal organs (including inguinal lymph nodes and lymph nodes outside of the abdominal cavity) |

Ovarian Cancer Grading

In addition to staging, an ovarian tumor can also be described by grade (G). Grading determines how similar ovarian cancer tissue is to normal tissue. Tumor grade is determined by microscopic examination of cancer tissue; with healthy cells appearing as well-differentiated. That is, the more differentiated the ovarian tumor, the better the prognosis. The ovarian cancer grading system is shown in Table 2.

TABLE 2

Ovarian Cancer Grading

| Grade | Description |
| --- | --- |
| GX | Grade cannot be evaluated |
| GB | Tissue considered borderline cancerous; low malignant potential |
| G1 | Tissue is well-differentiated (healthy cells) |
| G2 | Tissue is moderately differentiated (more abnormal than health cells) |
| G3 to G4 | Tissue is poorly differentiated or undifferentiated (all or most cells appear abnormal) |

Serous ovarian cancer is not graded in this way and only considers a low-grade and a high-grade classification. Low-grade serous carcinomas exhibit low-grade nuclei with infrequent mitotic figures. They evolve from adenofibromas or borderline tumors, have frequent mutations of the KRAS, BRAF, or ERBB2 genes, and lack TP53 mutations (Type I pathway). Low-grade tumors are indolent and have better outcome than high-grade tumors. In contrast, high-grade serous carcinomas have high-grade nuclei and numerous mitotic figures (See, Vang R. et al., Adv. Anat. Pathol. September 2009; 16(5):267-282).

Treatment for Ovarian Cancer

Early Stage (FIGO Stage I-II) Ovarian Cancer

Due to the lack of effective screening programs, ovarian cancer is diagnosed at an early stage only in about 25% of cases (Kim A. et al., Journal of Experimental & Clinical Cancer Research 2012, 31:14). In most of these cases, surgery is able to cure the disease, and the five-year survival rate for early-stage (stage I or II) ovarian cancer is around 90% (Hennessy B T, et al., Lancet 2009, 374: 1371-82). Adjuvant chemotherapy for early stage ovarian cancer is still controversial, but some studies have shown its benefit under confined conditions. According to these studies, patients with IA or IB FIGO stage, non-clear-cell histology, well-differentiated (G1) tumors, and an "optimal" surgery (i.e., performed according to international guidelines, with pelvic and retroperitoneal assessment), appear not to benefit from chemotherapy (Trimbos J B et al., J Natl Cancer Inst 2003, 95:105-112). Thus, it is commonly believed that, at least in these cases, chemotherapy can probably be avoided and patients can be advised to undergo clinical and instrumental follow-up. In all the other (early stage) patients, (adjuvant) chemotherapy is indicated (Hennessy B T, et al., Lancet 2009, 374: 1371-82).

Advanced (FIGO Stage III-IV) Ovarian Cancer

The standard treatment for patients with advanced ovarian cancer is maximal surgical cytoreduction (i.e., total abdominal hysterectomy, bilateral salpingo-oophorectomy, pelvic and para-aortic lymphadenectomy and omentectomy) followed by systemic platinum-based chemotherapy (e.g., cisplatin followed by carboplatin-based combinations, cisplatin with paclitaxel, cisplatin with cyclophosphamide, cisplatin with doxorubicin, etc.). The expected 5-year survival for these patients is 10-30% (Hennessey B T et al., Lancet 2009, 374:1371-82). The concept of primary debulking surgery is to diminish the residual tumor burden to a point at which adjuvant therapy will be optimally effective. The percentage of patients with advanced ovarian cancer who can optimally undergo cytoreductive surgery seems to range from 17%-87% (Ramirez I et al., Cancer Control 2011; 18(1): 22-30). This percentage can largely depend on the experience of the surgeon.

Novel Treatment Strategies for Ovarian Cancer

The larger expectation for improved prognosis in ovarian cancer is related to the use of new biological agents. A deeper knowledge of ovarian cancer biology has led to the identification of multiple molecular targets, such as growth factor receptors, signal transduction pathways, cell cycle regulators, and angiogenic mechanisms (Kim A et al., Journal of Experimental & Clinical Cancer Research 2012, 31:14).

Bevacizumab

Bevacizumab is a 149-kDa recombinant humanized monoclonal IgG1 directed against vascular endothelial growth factor (VEGF). It has been FDA-approved for the treatment of metastatic colorectal, breast, and non-small cell lung cancer and shows promise in the treatment of ovarian cancer. Several phase II studies have shown that bevacizumab is active in recurrent ovarian cancer (Ellis L M, Hiclin D J, Nat Rev Cancer 2008, 8:579-591; Raspollini M R et al., Int J Surg Pathol 2005, 13:135-142).

VEGF expression is higher in ovarian cancer tumors than in normal ovarian tissue or benign ovarian tumors, and increasing VEGF expression in either cytosolic fractions derived from ovarian cancer tumors or serum VEGF levels in preoperative serum is considered to be associated with advanced stage and poor prognosis (Kim A et al., Journal of Experimental & Clinical Cancer Research 2012, 31:14).

In order to inhibit the VEGF pathway, there are two primary strategies: (1) inhibition of the VEGF ligand with antibodies or soluble receptors and (2) inhibition of the VEGF receptor (VEGFR) with tyrosine kinase inhibitors (TKI5), or receptor antibodies. Of the VEGF targeting therapies, the one most employed has been inhibition of the VEGF ligand with bevacizumab) (Avastin®).

Two phase III trials (GOG218, ICON 7) have recently evaluated the role of bevacizumab in first-line chemotherapy as an adjunct to carboplatin and paclitaxel. Bevacizumab plus chemotherapy (carboplatin-paclitaxel) and bevacizumab maintenance was demonstrated to prolong progression-free survival (PFS) by about 4 months (10.3 months versus 14.1 months) compared to carboplatin-paclitaxel alone (Burger R A et al., N Engl J Med 2011, 365:2473-83; Perren T J et al., N Engl J Med 2011, 365:2484-96). A third trial (OCEANS trial) showed that the addition of bevacizumab prolonged PFS in platinum-sensitive recurrent ovarian carcinoma cases (Aghajanian C et al., J Clin Oncol 2011, 29).

VEGF Receptor Inhibitors

Oral inhibitors of the VEGF receptor (VEGFR) tyrosine kinase have been shown to have activity in patients with recurrent ovarian cancer, resulting in tumor responses and stabilization of disease, delaying tumor progression (Friedlander M et al., Gynecol Oncol 2010; 119:32-37; Ledermann J A et al., J Clin Oncol 2011; 29:3798-3804; Matulonis U A et al., J Clin Oncol 2009; 27:5601-5606; Biagi J J et al., Ann Oncol 2011; 22:335-340; Matei D et al., J Clin Oncol 2011; 29:69-75). Two agents are now in first-line studies. Pazopanib is an angiogenic inhibitor with broad spectrum activity against all three VEGF receptors, platelet derived growth factor receptor (PDGFR) and c-Kit that has been approved for use in first-line advanced renal cancer. Over 900 patients including a sub-set in Asia have been recruited to a maintenance study, in which patients receive pazopanib 800 mg daily or placebo until progression, or up to 2 years (aGO OVaR-16; trial NCT 00866697; 01227928). The primary end-point is PFS.

The second trial is with nintedanib (BIBF1120), a potent inhibitor of VEGFR/PDGFR and fibroblast growth factor receptor. In this trial, nintedanib or placebo is given with a standard regimen of carboplatin and paclitaxel after surgery and continued as maintenance therapy for up to 2 years (aGO OVaR-12 trial NCT01015118). This trial also has PFS as its primary end-point.

Targeting the angiopoietin axis is another strategy to develop anti-angiogenic therapy. aMG 386, a peptibody inhibiting the interaction of angiopoietin-1 and -2 to the Tie2 receptor, has been evaluated in combination with weekly paclitaxel in recurrent ovarian cancer [Karlan, B. Y. et al., J. Clin. Oncol. December 2011; doi: 10.1200/JCO.2010.34.3178]. The results of a phase II trial have been promising and have led to further exploration within the TRINOVa-3 trial of aMG 386/placebo plus carboplatin/paclitaxel in first-line ovarian cancer (NCT01493505).

Epidermal Growth Factor Receptor (EGFR) Inhibitors

The epidermal growth factor receptor (EGFR) is overexpressed in up to 70% of ovarian cancer patients (Kohler M et al., Eur J Cancer 1992; 28a:1432-1437). However, responses to EGFR inhibitors in recurrent ovarian cancer are infrequent, and, as with lung cancer, are dependent on the presence of a mutation in the catalytic domain of the EGFR (Schilder R J et al, Clin Cancer Res 2005; 11:5539-5584). Erlotinib is a highly potent oral inhibitor of the tyrosine kinase region of the EGFR, and this has been studied in a trial in which patients with high-risk stage I and stage II-IV epithelial ovarian cancer who had completed platinum-based chemotherapy were randomly assigned to erlotinib maintenance therapy or observation following chemotherapy.

Insulin Growth Factor (IGFR) Inhibitors

Insulin growth factor 1(IGF 1) is involved in the inhibition of apoptosis, tumor progression and metastases. aMG 479 is a monoclonal antibody that is a potent inhibitor of the IGF 1 receptor and OSI-906 is an oral dual kinase inhibitor of IGFR1 and the insulin receptor. The latter is in clinical trials in recurrent ovarian cancer. A randomized phase II study of aMG 479 added to first-line chemotherapy in patients with optimally debulked ovarian cancer is ongoing (NCT00718523).

Poly (ADP-ribose) Polymerase (PARP) Inhibitors

The poly (ADP-ribose) polymerases (PARPs) are a large family of multifunctional enzymes (Rouleau M et al., Nat Rev Cancer 2010, 10:293-301). PARP-1, the most abundant isoform, plays a key role in the repair of DNA single-strand breaks through the repair of base excisions. The inhibition of PARPs leads to the accumulation of DNA single-strand breaks, which causes DNA double-strand breaks at replication forks. These double-strand breaks are repaired in normal cells mainly by the error-free homologous recombination double-stranded DNA repair pathway, in which essential components are the tumor-suppressor proteins BRCA1 and BRCA2. In the absence of either BRCA1 or BRCA2, these lesions are not repaired, which results in cell cycle arrest and cell death (Itamochi H, World J Biol Chem 2010, 1:209-220).

Fong et al. (J Clin Oncol 2010, 28:2512-2519) administered the PARP inhibitor olaparib to platinum refractory patients. Olaparib had a favorable safety profile and a high response rate, in particular in patients with BRCA mutation. In patients with platinum-resistant and platinum-refractory disease, the response rate was 41.7% and 15.4%, respectively (Fong P C et al., J Clin Oncol 2010, 28:2512-2519). Olaparib (AZD2281) was tested in BRCA-mutated patients with ovarian, primary peritoneal, and fallopian tube cancer. In the study, 20 patients (40%) responded to the therapy. Currently, randomized trials of olaparib and other PARP inhibitors in patients with ovarian cancer are underway.

Biomarkers for Ovarian Cancer

Identification of early detection biomarkers for ovarian carcinoma remains a challenge due to a wide range of morphological, clinical, and genetic variations found in ovarian cancer progression (Bast R C Jr, Hennessy B, Mills G B. The biology of ovarian cancer: new opportunities for translation. Nat Rev Cancer 2009; 6:415-28). Currently available biomarkers lack specificity and sensitivity required for routine clinical use (Gubbels J A, Claussen N, Kapur A K, Connor J P, Patankar M S. The detection, treatment, and biology of epithelial ovarian cancer. J Ovarian Res 2010; 3:8). The only clinically validated biomarker used for early detection, disease monitoring, and assessing relapse or response to treatment is CA125; however, it has low specificity as a single marker and is not generally recommended for early detection (Karam A K, Karlan B Y. Ovarian cancer: the duplicity of CA125 measurement. Nat Rev Clin Oncol 2010; 7:335-9). Although its serum expression is elevated above normal in early stage (23%) and late stage (80%) disease, it lacks specificity and sensitivity for detection of ovarian cancer (Bast R C Jr, Urban N, Shidhar V, Smith D, Zhang Z, Skates S, et al. Early detection of ovarian cancer: promise and reality. Cancer Treat Res 2002; 107:61-97). The overexpression of CA125 is also frequently observed in benign conditions (e.g., endometriosis) and thus lacks accurate diagnostic value for early stage disease (Tuxen M K, Soletormos G, Dombernowsky P. Serum tumor marker CA-125 for monitoring ovarian cancer during follow-up. Scand J Clin Lab Invest 2002; 62:177-188). As an early detection biomarker of ovarian cancer, recent reports suggest that human epididymis protein 4 (HE4) provides greater sensitivity and specificity than CA125 (Anderson G L, McIntosh M, Wu L, Barnett M, Goodman G, Thorpe G, et al. Assessing lead time of selected ovarian cancer biomarkers: a nested case-control study. J Natl Cancer Inst 2010; 102:26-38; Hellstrom I, Hellstrom K E. SMRP and HE4 as biomarkers for ovarian carcinoma when used alone and in combination with CA125 and/or each other. Adv Exp Med Biol 2008; 622:15-21), and an assay that detects a combination of HE4, CA125, carcinoembryonic antigen (CEA), and vascular cell adhesion molecule 1 (VCAM-1) expression in serum has significantly better sensitivity to detect early stage ovarian cancer over benign tumors (Yurkovetsky Z, Skates S, Lomakin A, Nolen B, Pulsipher T, Modugno F, et al. Development of a multimarker assay for early detection of ovarian cancer. J Clin Oncol 2010; 28:2159-66; Nolen B, Velikokhatnaya L, Marrangoni A, De Geest K, Lomakin A, Bast R C, et al. Serum biomarker panels for the discrimination of benign from malignant cases in patients with an adnexal mass. Gynecol Oncol. 2010; 117:440-5). In addition, the Food and Drug Administration (FDA) has approved an OVA1 test consisting of a panel of five biomarkers: transthyretin, apolipoprotein A-1, beta2-microglobulin, transferrin, and CA125 (Zhang Z, Chan D W. The road from discovery to clinical diagnostics: lessons learned from the first FDA-cleared in vitro diagnostic multivariate index assay of proteomic biomarkers. Cancer Epidemiol Biomarkers Prev 2010; 19:2995-9). This suggests that use of a combination of multiple markers may generate synergistic advantages over single marker diagnostics. Although the multimarker OVA-1 test demonstrates a much higher detection sensitivity than a test for CA-125 alone, it is most efficient in detection of advanced-stage ovarian cancer and was FDA-cleared for pre-surgical evaluation of women already possessing an ovarian mass.

Kallikrein Family of Serine Proteases

A number of human kallikrein (KLK) family members are associated with human cancers and exhibit differential expression in many types of advanced cancers, including gastrointestinal, head and neck, lung, ovarian, and brain (Donach M, Yu Y, Artioli G, Banna G, Feng W, Bast R C Jr, Combined use of biomarkers for detection of ovarian cancer in high-risk women. Tumour Biol 2010; 31:209-15; McIntosh M W, Liu Y, Drescher C, Urban N, Diamandis E P. Validation and characterization of human kallikrein 11 as a serum marker for diagnosis of ovarian carcinoma. Clin Cancer Res 2007; 13:4422-8; Shan S J, Scorilas A, Katsaros D, Rigault de la Longrais I, Massobrio M, et al. Unfavorable prognostic value of human kallikrein 7 quantified by ELISA in ovarian cancer cytosols. Clin Chem 2006; 52:1879-86), however no previous reports to date have focused on detection of early stage ovarian cancer, specifically by measuring levels of KLK6 and/or KLK7. In a study by El Sherbini et al., 40% of stage I/II patients (n=10-15) presented above-normal levels of KLK6 while 83.3% of stage III/IV patients (N=12) were KLK6 positive (El-Sherbini et al. Diagnostic value of serum kallikrein-related peptidases 6 and 10 versus CA125 in ovarian cancer, Int. J. Gyn. Cancer 2011, 21(4): 625-632). Although this study demonstrated that KLK6 has a better sensitivity than CA-125 as an early detection biomarker, it included serum tests only (El-Sherbini et al. Diagnostic value of serum kallikrein-related peptidases 6 and 10 versus CA125 in ovarian cancer, Int. J. Gyn. Cancer 2011, 21(4): 625-632).

The human KLK family comprises 15 homologous secreted trypsin- or chymotrypsin-like serine proteases, encoded by tightly clustered genes found in the chromosome 19q13.4 region (Sotiropoulou G, Pampalakis G. Kallikrein-related peptidases: bridges between immune functions and extracellular matrix degradation. Biol Chem 2010; 391:321-31). Kallikrein transcription is regulated by many stimulatory and inhibitory factors, including steroid hormones (Lawrence M G, Lai J., Clements J A. Kallikreins on Steroids: Structure, Function, and Hormonal Regulation of Prostate-Specific Antigen and the Extended Kallikrein Locus. Endocr Rev 2010; 31:407-46). The KLKs are co-expressed in the epithelia of several organs and mediate a range of physiological functions, including skin desquamation and body fluid homeostasis (Emami N, Diamandis E P. New insights into the functional mechanisms and clinical applications of the kallikrein-related peptidase family. Mol Oncol 2007; 1:269-87). A number of studies have found that KLK genes/proteins are aberrantly expressed in multiple human cancers, and their overexpression in late stage tumors is often associated with unfavorable patient prognosis (Mavridis K, Scorilas A. Prognostic value and biological role of the kallikrein-related peptidases in human malignancies. Future Oncol 2010; 6:269-85; Nathalie H V, Chris P, Serge G, Catherine C, Benjamin B, Claire B, et al. High kallikrein-related peptidase 6 in non-small cell lung cancer cells: an indicator of tumour proliferation and poor prognosis. J Cell Mol Med 2009; 13:4014-22; Nagahara H, Mimori K, Utsunomiya T, Barnard G F, Ohira M, Hirakawa K, et al. Clinicopathologic and biological significance of kallikrein 6 overexpression in human gastric cancer. Clin Cancer Res 2005; 11:6800-6). Expression is associated with cancer cell growth, angiogenesis, invasion, and metastasis by proteolytic processing of signaling proteins and extracellular matrix components (Paliouras M, Diamandis E P. The kallikrein world: an update on the human tissue kallikreins. Biol Chem 2006; 387:643-52). Similarly, elevated KLK expression has been reported in late stage ovarian cancer (Karp P D, Paley S, Krieger C J, Zhang P. An evidence ontology for use in pathway/genome databases. Pac Symp Biocomput 2004:190-201); however, its expression or role in the early stages of disease has not been extensively studied.

Kallikrein 6 and Kallikrein 7

The kallikrein 6 (KLK6) protein is normally expressed as a proenzyme in multiple adult tissues. KLK6 protein is activated by cleavage by other proteases and then secreted into biological fluids (Blaber S I, Yoon H, Scarisbrick I A, Juliano M A, Blaber M. The autolytic regulation of human kallikrein-related peptidase 6. Biochemistry 2007; 46:5209-17; Oikonomopoulou K, Batruch I H, Smith C R, Soosaipillai A, Diamandis E P, Hollenberg M D. Functional proteomics of kallikrein-related peptidases in ovarian cancer ascites fluid. Biol Chem 2010; 391:381-90). Mature KLK6 degrades basic constituents of the extracellular matrix and basement membrane in tissues (Borgoño C A, Diamandis E P. The emerging roles of human tissue kallikreins in cancer. Nat Rev Cancer 2004; 4:876-90). In advanced ovarian cancers, overexpression of this protease, among others, has been associated with shorter disease-free survival and overall survival (Prezas P, Arlt M J, Viktorov P, Soosaipillai A, Holzscheiter L, Schmitt M, et al. Overexpression of the human tissue kallikrein genes KLK4, 5, 6, and 7 increases the malignant phenotype of ovarian cancer cells. Biol Chem 2006; 387:807-11). In addition, overexpression of KLK6 in ovarian cancer cell lines leads to transformation to a malignant cell phenotype (Prezas P, Arlt M J, HViktorov P, Soosaipillai A, Holzscheiter L, Schmitt M, et al. Overexpression of the human tissue kallikrein genes KLK4, 5, 6, and 7 increases the malignant phenotype of ovarian cancer cells. Biol Chem 2006; 387:807-11). The combination of KLK6 and KLK13 overexpression has been associated with tumor recurrence (White N M, Mathews M, Yousef G M, Prizada A, Popadiuk C, Doré J J. KLK6 and KLK13 predict tumor recurrence in epithelial ovarian carcinoma. Br J Cancer 2009; 101:1107-13).

Similarly, kallikrein 7 (KLK7) (also known as stratum corneum chymotryptic enzyme) is overexpressed in human cancers and is secreted into bodily fluids (Kyriakopoulou L G, Yousef G M, Scorilas A, Katsaros D, Massobrio M, Fracchioli S, et al. Prognostic value of quantitatively assessed KLK7 expression in ovarian cancer. Clin Biochem 2003; 36:135-43; Shaw J L, Diamandis E P. Distribution of 15 human kallikreins in tissues and biological fluids. Clin Chem 2007; 53:1423-32). Overexpression of KLK7 in ovarian carcinoma cells results in the formation of multicellular aggregates and promotes chemoresistance (Dong Y, Tan O L, Loessner D, Stephens C, Walpole C, Boyle G M, et al. Kallikrein-related peptidase 7 promotes multicellular aggregation via the alpha(5)beta(1) integrin pathway and paclitaxel chemoresistance in serous epithelial ovarian carcinoma. Cancer Res 2010; 70:2624-33).

In relation to the clinicopathology of tumor progression, maintaining overexpression of both KLK6 and KLK7 has strong implications in tumor metastasis. KLK6 and KLK7 enzymatically target several major extracellular proteins, such as fibronectin, laminin, other structural proteins related to myelin basic protein, gelatin and casein (Sotiropoulou G, Pampalakis G, Diamandis E P. Functional roles of human kallikrein-related peptidases. J Biol Chem 2009; 284:32989-94). It has been hypothesized that the known activity of KLK7 in the desquamation of cornified layers in normal skin may be similar to its role in metastasis (Eissa A, Diamandis E P. Human tissue kallikreins as promiscuous modulators of homeostatic skin barrier functions. Biol Chem 2008; 389: 669-80).

Prostasin (PRSS8)

Prostasin (PRSS8), a trypsin-like proteinase (40 kDa), is a glycosyl-phosphatidyl-inositol (GPI)-anchored extracellular serine protease that is localized on chromosome 16p11.2. Prostasin was first isolated from seminal fluid and is normally produced by the prostate gland (Yu, J. X., L. Chao, and J. Chao, Prostasin is a novel human serine proteinase from seminal fluid. Purification, tissue distribution, and localization in prostate gland. J Biol Chem, 1994. 269(29): p. 18843-8). Its expression was demonstrated in epithelial cells and the ducts of the prostate (Yu 1994), and it is also present in low levels on the apical surface of epithelial tissues such as lung, kidney, liver, bronchi, colon and salivary glands, indicating that it may have roles in multiple biological processes (Costa, F. P., et al., Prostasin, a potential tumor marker in ovarian cancer—a pilot study. Clinics (Sao Paulo), 2009. 64(7): p. 641-4). PRSS8 is present in multiple tissues that absorb sodium (Planes, C., et al., ENaC-mediated alveolar fluid clearance and lung fluid balance depend on the channel-activating protease 1. EMBO Mol Med, 2010. 2(1): p. 26-37). It acts as a proteolytic activator of the epithelial sodium channel in vitro, and thus is thought to play a major role in regulating sodium balance (Vallet, V., et al., An epithelial serine protease activates the amiloride-sensitive sodium channel. Nature, 1997. 389(6651): p. 607-10; Vuagniaux, G., et al., Synergistic activation of ENaC by three membrane-bound channel-activating serine proteases (mCAP1, mCAP2, and mCAP3) and serum- and glucocorticoid-regulated kinase (Sgkl) in Xenopus Oocytes. J Gen Physiol, 2002. 120(2): p. 191-201; Vuagniaux, G., et al., Activation of the amiloride-sensitive epithelial sodium channel by the serine protease mCAP1 expressed in a mouse cortical collecting duct cell line. J Am Soc Nephrol, 2000. 11(5): p. 828-34). PRSS8 is over-expressed in many cancer types such as urinary bladder, uterus, prostate and ovarian, compared to its level in the corresponding normal tissue (Mitsui, S., et al., A novel serine protease highly expressed in the pancreas is expressed in various kinds of cancer cells. FEBS J, 2005. 272(19): p. 4911-23; Ovaere, P., et al., The emerging roles of serine protease cascades in the epidermis. Trends Biochem Sci, 2009. 34(9): p. 453-63; Selzer-Pion, J., et al., Expression of prostasin and its inhibitors during colorectal cancer carcinogenesis. BMC Cancer, 2009. 9: p. 201). However, its activation of epithelial sodium channels suppresses the in vitro invasiveness of both prostate and breast cancer (Yu, J. X., L. Chao, and J. Chao, Prostasin is a novel human serine proteinase from seminal fluid. Purification, tissue distribution, and localization in prostate gland. J Biol Chem, 1994. 269(29): p. 18843-8; Yu, J. X., et al., Structure and chromosomal localization of the human prostasin (PRSS8) gene. Genomics, 1996. 32(3): p. 334-40; Verghese, G. M., M. F. Gutknecht, and G. H. Caughey, Prostasin regulates epithelial monolayer function: cell-specific Gpld1-mediated secretion and functional role for GPI anchor. Am J Physiol Cell Physiol, 2006. 291(6): p. C1258-70). It was found that in bladder cancer, loss of prostasin is associated with EMT—epithelial to mesenchymal transition—a process during which epithelial cells are converted to migratory and invasive cells (Chen et al, BMC cancer 2009, 9: 377). However, the role of prostasin in ovarian cancer is not understood (Dorn J. et al., Crit Rev Clin Lab Sci. 2014 Apr., 51(2): 63-84).

It has been shown that prostasin down-regulates epidermal growth factor receptor (EGFR) protein expression and epidermal growth factor (EGF)-induced phosphorylation of Erk1/2 in PC-3 prostate cancer cells, and it has been suggested that PRSS8 also cleaves the extracellular domain of the epithelial EGFR. The cleaved receptor remains continuously phosphorylated and can potentially trigger metastasis. Moreover, levels of PRSS8 in ovarian carcinoma cell lines and in the serum of ovarian cancer patients have been shown to be elevated (Costa, F. P., et al., Prostasin, a potential tumor marker in ovarian cancer—a pilot study. Clinics (Sao Paulo), 2009. 64(7): p. 641-4).

Interest in using prostasin as a potential biomarker for ovarian cancer was generated by several studies that demonstrated that prostasin is up-regulated in ovarian cancer tissues. In a study by Mok et al., serum prostasin was measured by microarray technology in 64 ovarian cancer patients and in 137 normal individuals. The serum prostasin mean level of detection was 13.7 µg/ml in all ovarian cancer patients compared to 7.5 µg/ml in all control subjects. As a result, sensitivity and specificity of prostasin as a biomarker was calculated as high as 92% and 94%, respectively. Moreover, post-operation levels of PRSS8 in the majority of the patients posted a significant decline, indicating that PRSS8 may be potentially used not only as a diagnostic but also as a prognostic biomarker (Mok, S. C., et al., Prostasin, a potential serum marker for ovarian cancer: identification through microarray technology. J Natl Cancer Inst, 2001. 93(19): p. 1458-64). Similarly, in a study by Costa et. al., levels of PRSS8 mRNA were evaluated in 12 ovarian cancer patients by RT-PCR and immune-staining relative to the levels of PRSS8 expression in normal prostate tissues. Costa et al. demonstrated that PRSS8 levels were 120 to 410-fold higher in ovarian cancer patients compared to normal controls (Costa, F. P., et al., Prostasin, a potential tumor marker in ovarian cancer—a pilot study. Clinics (Sao Paulo), 2009. 64(7): p. 641-4). In another study, PRSS8 levels in ovarian cancer cell lines were shown to be linked to regulation by zinc-finger protein 217 (ZNF217), a protein commonly over-expressed during cancer progression that promotes tumor-cell survival. By using Affymetrix Gene Chip analysis in the ovarian cancer cell line HO-8910, silencing of the ZNF217 gene was observed, which resulted in nearly an 8-fold down-regulation of 164 genes compared to non-silenced control cells, including PRSS8 and WAP four-disulfide core domain 2 (WFDC2), also known as human epididymis protein 4 (HE4), which is currently used as an early detection biomarker for ovarian cancer (Sun, G., et al., Microarray analysis of gene expression in the ovarian cancer cell line HO-8910 with silencing of the ZNF217 gene. Mol Med Rep, 2009. 2(5): p. 851-5). Results from these studies placed prostasin on the list of potential biomarkers for early detection of ovarian cancer (Rein et al., Journal of Oncology 2011, Article ID 475983, 17 pages).

Although these studies seemed to demonstrate that PRSS8 is upregulated in early-stage ovarian cancer (Costa, F. P., et al., Prostasin, a potential tumor marker in ovarian cancer—a pilot study. Clinics (Sao Paulo); Mok, S. C., et al., Prostasin, a potential serum marker for ovarian cancer: identification through microarray technology. J Natl Cancer Inst, 2001. 93(19): p. 1458-64), interest in this protein as a potential biomarker has waned, primarily due to studies which showed opposing results. For example, Chien et al. observed that prostasin was not among 61 genes that were overexpressed in stage I high grade carcinoma (Chien J. et al., Gynecologic Oncology 2009 July; 114(1): 3-11). In another study, over 40,000 genes were analyzed in genome arrays of epithelial tissues obtained from ovarian cancer patients in different grades, stages and subtypes of the disease, and compared to an analysis of normal ovarian tissue. PRSS8 was not among the genes that were expressed at least 3-fold higher in ovarian cancer tissues vs. normal tissues, nor was it among the genes that were part of a combination of genes which could detect all cancer cases (Lu K. H. et al, Clin Cancer Res. May 15, 2004 10; 3291).

There is a need for biomarkers useful in the early detection of ovarian carcinoma. The described invention provides three such biomarkers. Specifically, mRNA and protein levels of KLK6, KLK7 and PRSS8 are significantly elevated both in ovarian cancer tissue and in serum in early stage ovarian cancer. Because KLK6, KLK7 and PRSS8 mRNA and protein can be detected in serum, subjects with elevated levels of expression of these markers in serum are appropriate candidates for also obtaining and analyzing a tissue sample for measuring the level of expression of KLK6, KLK7 and PRSS8. When both tissue and serum are positive for these markers, an early diagnosis and early treatment is possible.

SUMMARY OF THE INVENTION

The described invention provides methods for detecting, diagnosing and treating early stage (I/II) ovarian cancer.

According to one aspect, the described invention provides a method for detecting, diagnosing and treating early stage (I/II) ovarian cancer in a subject comprising: (a) obtaining a serum sample from the subject and obtaining a normal serum control sample; (b) isolating from the sample obtained in (a) total RNA comprising a serine protease mRNA, wherein the serine protease is at least 2 selected from the group consisting of kallikrein 6 (KLK6), kallikrein 7 (KLK7), and PRSS8; (c) transforming the isolated total RNA of (b) into cDNA comprising serine protease cDNA; (d) amplifying the cDNA of (c); (e) measuring a level of amplified serine protease cDNA in (d) as a measure of expression of amplified serine protease mRNA; (f) comparing the level of expression of the amplified serine protease mRNA in (e) expressed by the subject with the level of expression of the amplified serine protease mRNA in (e) expressed by the normal serum control sample, wherein an increased level of expression of the serine protease mRNA expressed by the subject compared to the level of expression of the serine protease mRNA expressed by the normal serum control sample is indicative of possible early stage ovarian cancer in the subject; (g) when (f) is indicative of early stage (I/II) ovarian cancer in the subject, obtaining an ovarian tissue sample from the subject; (h) isolating from the ovarian tissue sample obtained in (g) total RNA comprising serine protease mRNA; (i) transforming the isolated total RNA of (h) into cDNA comprising serine protease cDNA; (j) amplifying the cDNA of (i); (k) measuring a level of amplified serine protease cDNA in (j) as a measure of expression of amplified serine protease mRNA; (l) comparing the level of expression of the amplified serine protease mRNA in (k) expressed by the subject with the level of expression of the amplified serine protease mRNA in (k) expressed by a normal ovarian tissue control sample, wherein an increased level of expression of the serine protease mRNA expressed by the subject compared to the level of expression of the serine protease mRNA expressed by the normal ovarian tissue control sample is indicative of possible early stage ovarian cancer in the subject; (m) when both (f) and (l) are indicative of early stage ovarian cancer, diagnosing early stage (I/II) ovarian cancer in the subject; and (n) treating the subject with a treatment regimen effective to treat the early stage (I/II) ovarian cancer.

According to another aspect, the described invention provides a method for detecting, diagnosing and treating early stage (I/II) ovarian cancer in a subject comprising: (a) obtaining a serum sample from the subject and a normal serum sample as a control; (b) detecting serine protease protein in the samples from (a) by reacting an anti-serine protease antibody with the patient serum sample and the normal serum control sample, wherein the serine protease is at least 2 selected from the group consisting of kallikrein 6 (KLK6), kallikrein 7 (KLK7), and PRSS8; (c) quantifying an amount of serine protease protein bound by the anti-serine protease antibody in (b); (d) comparing the amount of serine protease protein in (c) bound by antibody in the subject serum sample with the amount of the serine protease protein bound by antibody in the normal serum control sample, wherein an increased amount of the serine protease protein bound in the subject sample compared to the amount of the serine protease protein bound in the normal serum control sample is indicative of early stage (I/II) ovarian cancer in the subject; (e) when (d) is indicative of ovarian cancer in the subject, obtaining an ovarian tissue sample from the subject and a normal ovarian tissue sample as a control; (f) detecting serine protease protein in the samples from (e) by reacting an anti-serine protease antibody with the subject ovarian tissue sample and the normal ovarian tissue sample; (g) quantifying an amount of serine protease protein bound by the anti-serine protease antibody in (f); (h) comparing the amount of serine protease protein bound in the subject ovarian tissue sample with the amount of the serine protease protein bound in the normal ovarian tissue control sample, wherein an increased amount of the serine protease protein bound in the subject ovarian tissue sample compared to the amount of the serine protease protein bound in the normal ovarian tissue control sample is indicative of early stage (I/II) ovarian cancer in the subject; (i) when both (d) and (h) are indicative of early stage ovarian cancer, diagnosing early stage (I/II) ovarian cancer in the subject; and (j) treating the subject with a treatment regimen effective to treat ovarian cancer.

According to one embodiment, the ovarian tissue sample is epithelial.

According to another embodiment, the normal serum control sample is a pooled normal serum sample.

According to one embodiment, the amplifying is performed by Reverse-Transcriptase-Polymerase Chain Reaction (RT-PCR).

According to one embodiment, the detecting is performed by Western blot or immunohistochemistry.

According to one embodiment, the ovarian cancer is selected from the group consisting of serous, papillary serous, metastatic, borderline, mucinous and clear cell.

According to one embodiment, the ovarian cancer is a grade 1 ovarian cancer characterized by: (i) well-differentiated tissue; or (ii) low grade nuclei with infrequent mitotic figures. According to another embodiment, the ovarian cancer is a stage I ovarian cancer characterized by: (i) a tumor limited to one ovary, capsule intact, no tumor on ovarian surface and negative washings (Stage IA); (ii) a tumor involving both ovaries, capsule intact, no tumor on ovarian surface and negative washings (Stage IB); (iii) surgical spill (Stage IC1); (iv) capsule rupture before surgery or tumor on ovarian surface (Stage IC2); or (v) malignant cells in ascites or in peritoneal washings (Stage IC3). According to another embodiment, the ovarian cancer is a stage II ovarian cancer characterized by: (i) extension and/or implant of a tumor on uterus and/or Fallopian tubes (Stage IIA); or (ii) extension of a tumor to other pelvic intraperitoneal tissues (Stage IIB).

According to one embodiment, the increased level of expression of the serine protease mRNA expressed by the subject compared to the level of expression of the serine protease mRNA expressed by the normal ovarian tissue control sample is indicative of an expansion of tumor epithelial compartment cells. According to another embodiment, the increased level of serine protease protein expressed by the subject compared to the level of expression of the serine protease protein expressed by the normal ovarian tissue control sample is indicative of an expansion of tumor epithelial compartment cells.

BRIEF DESCRIPTION OF THE DRAWINGS

For a more complete understanding of the present disclosure, reference is made to the following detailed description of exemplary embodiments considered in conjunction with the accompanying drawings.

FIG. 12A1a: normal ovary tissue array; FIG. 12A1b: stained for PRSS8; FIG. 12A2a:serous adenocarcinoma with negative control; 12A2b: stained for PRSS8; FIG. 12A3a: endometriod adenocarcinoma with negative control; 12A3b: stained for PRSS8; FIG. 12A4a: serous cystadenoma with negative control; 12A4b: stained for PRSS8; B1: benign ovary tissue; C1: serous adenocarcinoma various tissue arrays; C2: papillary serous adenocarcinoma various tissue arrays; C3: mucinous adenocarcinoma various arrays; C4: endometriod adenocarcinoma; C5: clear cell various arrays; C6: borderline carcinoma; C7: transitional cell carcinoma; D1 and D2: cancer (non-OVC); E1: Bar plots of PRSS8 immunostaining score by OVC stage; and E2: Bar plots of PRSS8 immunostaining score by OVA grade. n=number of stained arrays in each group.

DETAILED DESCRIPTION OF THE INVENTION

Figure 1:
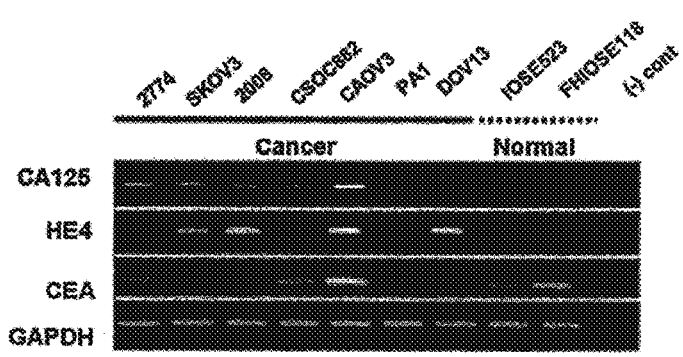
FIG. 1 shows overexpression of KLK6 and KLK7 genes in ovarian cancer cell lines. (A) Established ovarian cancer cell lines representing different age, stage, and subtypes were selected and tested for expression of known ovarian cancer genes (CA125, HE4, and CEA) by end-point PCR relative to normal ovarian epithelial cell lines. Amplified DNAs were qualitatively compared following electrophoretic separation as ethidium bromide-stained bands on agarose gels. (B) Gene expression of KLK6 and KLK7 in ovarian cancer cell lines (solid black bars) and normal ovary cell lines (N) was analyzed by qRT-PCR and normalized against a "primary-like" normal ovarian cell line (IOSE523; solid gray bar). IOSE523 begins to senesce after twenty passages while FIOSE118 is immortal. The mean fold change represents triplicate measurements, and the standard error bars are shown.
Figure 1:
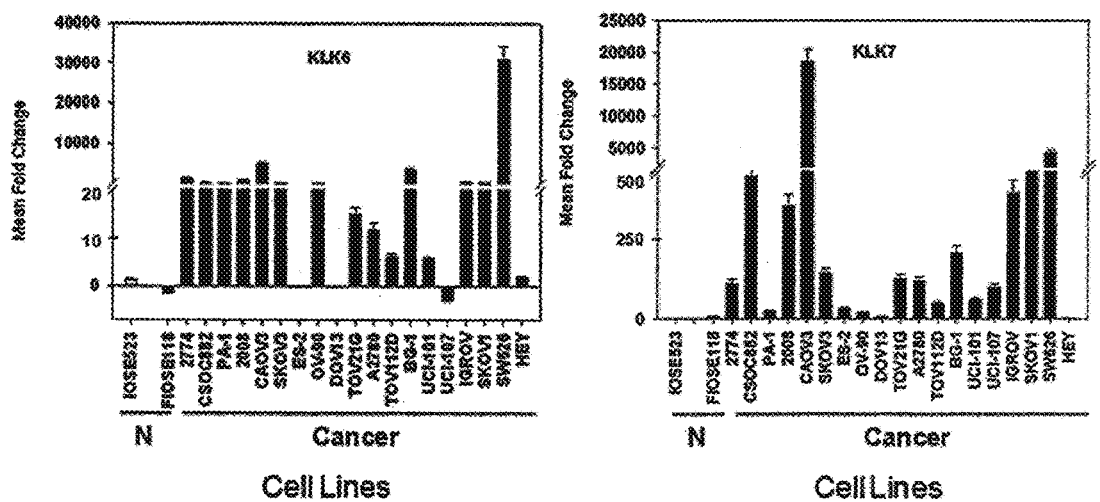

The described invention can be better understood from the following description of exemplary embodiments, taken in conjunction with the accompanying figures and drawings. It should be apparent to those skilled in the art that the described embodiments of the described invention provided herein are merely exemplary and illustrative and not limiting.

Definitions

Various terms used throughout this specification shall have the definitions set out herein.

The term "biomarker" (or "biosignature") as used herein refers to a peptide, a protein, a nucleic acid, an antibody, a gene, a metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. The term "cancer biomarker" (or "cancer biosignature") as used herein refers to a peptide, a protein, a nucleic acid, an antibody, a gene, a metabolite, or any other substance used to detect the predisposition for, or the presence of, primary or metastatic cancer in a subject. According to the described invention, biomarkers useful in the detection of ovarian cancer include, but are not limited to, KLK6, KLK7 and PRSS8.

The phrases "borderline tumor", "borderline cancer", "borderline ovarian tumor" and "borderline ovarian cancer" are used interchangeably herein to refer to a group of tumors that, in contrast to typical ovarian carcinomas, do not invade the ovarian stroma and therefore are considered noninvasive. Borderline tumors have a superior prognosis when compared with other ovarian carcinomas stage for stage.

The term "cDNA" refers to DNA synthesized from a mature mRNA template. cDNA most often is synthesized from mature mRNA using the enzyme reverse transcriptase. The enzyme operates on a single strand of mRNA, generating its complementary DNA based on the pairing of RNA base pairs (A, U, G, C) to their DNA complements (T, A, C, G). There are several methods known for generating cDNA to obtain, for example, eukaryotic cDNA whose introns have been spliced. Generally, these methods incorporate the following steps: a) a eukaryotic cell transcribes the DNA (from genes) into RNA (pre-mRNA); b) the same cell processes the pre-mRNA strands by splicing out introns, and adding a poly-A tail and 5' Methyl-Guanine cap; c) this mixture of mature mRNA strands is extracted from the cell; d) a poly-T oligonucleotide primer is hybridized onto the poly-A tail of the mature mRNA template (reverse transcriptase requires this double-stranded segment as a primer to start its operation); e) reverse transcriptase is added, along with deoxynucleotide triphosphates (A, T, G, C); f) the reverse transcriptase scans the mature mRNA and synthesizes a sequence of DNA that complements the mRNA template. This strand of DNA is complementary DNA (cDNA).

The term "cell" is used herein to refer to the structural and functional unit of living organisms and is the smallest unit of an organism classified as living.

The term "condition" as used herein, refers to a variety of health states and is meant to include disorders or diseases caused by injury or any underlying mechanism or disorder.

The term "disease" or "disorder" as used herein refers to an impairment of health or a condition of abnormal functioning.

The term "gene" as used herein refers to a region of DNA that controls a discrete hereditary characteristic, usually corresponding to a single protein or RNA. This definition includes the entire functional unit, encompassing coding DNA sequences, noncoding regulatory DNA sequences and introns.

The term "hybridization" refers to the process of combining complementary, single-stranded nucleic acids into a single molecule. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed. The term "specifically hybridizes" as used herein refers to the process whereby a nucleic acid distinctively or definitively forming base pairs with complementary regions of at least one strand of DNA that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 90% sequence identity, or at least 100% sequence identity (i.e., complementary) with each other.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated, separate from its natural environment.

The term "kallikrein" as used herein refers to a member of the S1 family (clan SA) of trypsin-like serine proteases. Kallikrein proteins are encoded by 15 structurally similar, steroid hormone regulated genes (KLK) that co-localize to chromosome 19q13.4. Kallikrein proteins are implicated in a wide range of physiologic functions such as blood pressure regulation, electrolyte balance, tissue remolding, pro-hormone processing, neural plasticity and skin desquamation.

The terms "kallikrein 6", "kallikrein-6", and "KLK6" are used interchangeably herein to refer to a member of the kallikrein family of serine proteases. The KLK6 gene comprises 11,043 nucleotides that encode a protein 244 amino acids in length. The KLK6 protein acts upon amyloid precursor protein, myelin basic protein, gelatin, casein, extracellular matrix proteins (e.g., fibronectin, laminin, vitronectin and collagen); degrades a-synuclein and prevents its polymerization; and regulates axon outgrowth following spinal cord injury.

The terms "kallikrein 7", "kallikrein-7", and "KLK7" used interchangeably herein refer to a member of the kallikrein family of serine proteases. The KLK7 gene comprises 7,627 nucleotides that encode a protein 253 amino acids in length. The KLK7 protein catalyzes the degradation of intercellular cohesive structures in the cornified layer of the skin and is implicated in the activation of precursors to inflammatory cytokines.

The terms "metastasis" or "metastases" as used herein refer to tumor growth or deposit that has spread via lymph or blood to an area of the body remote from the primary tumor.

The term "metastasize" as used herein refers to the spread of cancer from one part of the body to another. A tumor formed by cells that have spread is called a "metastatic tumor" or "metastasis." The plural form of "metastasis" is "metastases."

The term "nucleic acid" as used herein refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" as used herein refers to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "peptide" is used herein to refer to two or more amino acids joined by a peptide bond.

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The terms "poor clinical outcome", "poor outcome" or "PO" are used interchangeably herein to refer to chemo-naïve primary refractory or early relapsing and chemo-exposed, multiple relapse within four (4) years or shortened survival/death two (2) to three (3) years after diagnosis.

The term "primer" refers to a nucleic acid which, when hybridized to a strand of DNA, is capable of initiating the synthesis of an extension product in the presence of a suitable polymerization agent. The primer is sufficiently long to uniquely hybridize to a specific region of the DNA strand. A primer also may be used on RNA, for example, to synthesize the first strand of cDNA.

The term "progression" as used herein refers to the course of a disease, such as ovarian cancer, as it becomes worse or spreads in the body.

The term "progression free survival" or "PFS" as used herein refers to a length of time during and after the treatment of a disease, such as cancer, that a patient lives with the disease but it does not get worse. In a clinical trial, measuring the progression free survival is one way to determine how well a new treatment works.

The term "protein" is used herein to refer to a large complex molecule or polypeptide composed of amino acids. The sequence of the amino acids in the protein is determined by the sequence of the bases in the nucleic acid sequence that encodes it.

The terms "PRSS8", "Prostasin", "Protease, Serine, 8", "Serine Protease 8", "Channel-activating Protease 1" and "CAP1" are used interchangeably herein to refer to a member of the trypsin family of serine proteases. The PRSS8 gene comprises 4,398 nucleotides that encode a protein 343 amino acids in length. The PRSS8 protein possesses a trypsin-like cleavage specificity with a preference for polybasic substrates. The proprotein is cleaved to produce a light chain and a heavy chain which are associated by a disulfide bond. The PRSS8 protein stimulates epithelial sodium channel (ENaC) activity via activating cleavage of the gamma subunits. PRSS8 shares sequence homology at the amino acid level with acrosin, plasma kallikrein, hepsin, testisin and gamma tryptase.

The term "quality of life" as used herein refers to the overall enjoyment of life, including aspects of an individual's sense of well-being and ability to carry out various activities.

The terms "recurrence" or "relapse" are used interchangeably herein to refer to the return of a cancer after a first-line treatment and after a period of time during which the cancer cannot be detected.

The term "refractory" as used herein refers to cancer that does not respond to treatment. The cancer may be resistant at the beginning of treatment or it may become resistant during treatment. The term "primary refractory" as used herein refers to the progression of disease during induction treatment or a partial or transient response (e.g. less than 60 days) to induction therapy. The term "induction therapy" as used herein refers to the first treatment given for a disease which is often part of a standard set of treatments, for example, surgery followed by chemotherapy and radiation. Induction therapy is often accepted as the best treatment option. Induction therapy is also known as "first-line therapy," "primary therapy" and "primary treatment."

The term "relapse-free survival (RFS)" as used herein refers to the length of time after primary treatment for a cancer during which the patient survives without any signs or symptoms of that cancer. It is also called disease-free survival (DFS).

The term "relative" as used herein refers to something having, or standing in, some significant association to something else. The term "relative frequency" as used herein refers to the rate of occurrence of something having or standing in some significant association to the rate of occurrence of something else. For example, two cell types, X cells and Y cells occupy a given location. There are 5 X cells and 5 Y cells in that location. The relative frequency of cell type X is 5/10; the relative frequency of cell type Y is 5/10 in that location. Following processing, there are 5 X cells, but only 1 Y cell in that location. The relative frequency of cell type X following processing is 5/6, and the relative frequency of cell type Y following processing is 1/6 in that location.

The term "risk factor" as used herein refers to anything that raises the chances of a person developing a disease.

The terms "subject" and "patient" are used interchangeably herein to refer to animal species of mammalian origin that may benefit from the administration of a drug composition or method of the described invention. Examples of subjects include humans, and other animals such as horses, pigs, cattle, dogs, cats, rabbits, mice, rats and aquatic mammals.

The term "syndrome" as used herein, refers to a pattern of symptoms indicative of some disease or condition.

Tissue Compartments.

In multicellular organisms, cells that are specialized to perform common functions are usually organized into cooperative assemblies embedded in a complex network of secreted extracellular macromolecules, the extracellular matrix (ECM), to form specialized tissue compartments. Individual cells in such tissue compartments are in contact with ECM macromolecules. The ECM helps hold the cells and compartments together and provides an organized lattice or scaffold within which cells can migrate and interact with one another. In many cases, cells in a compartment can be held in place by direct cell-cell adhesions. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

The term "tumor epithelial compartment cells" as used herein refers to tumor cells arising from cells in the epithelial compartment that form the epithelium. The epithelium is a layer of cells that covers the internal and external organs of the body, that lines vessels, body cavities, glands and organs, that forms the epidermis of the skin and the surface layer of mucus and serous membranes. Epithelial cells rest on a basement membrane and lie in close proximity with little intercellular material between them. Epithelial cells are devoid of blood vessels and may be simple (consisting of a single layer) or stratified (consisting of several layers). Cells comprising the epithelium may be flat (squamous), cube-shaped (cuboidal) or cylindrical (columnar). Modified forms of epithelium include, but are not limited to, ciliated (hair-like processes on the surface), pseudostratified (appears stratified because cells are arranged with their nuclei at different levels), glandular (composed of secreting cells) and neuroepithelium (composed of sensory cells). The epithelium may include goblet cells which secrete mucus. Squamous epithelium is classified as endothelium, which lines the blood vessels and heart, and mesothelium, which lines the serous cavities. Functions of the epithelium include, but are not limited to, protection, absorption, secretion, movement of substances through ducts, production of germ cells and reception of stimuli.

The Tumor Microenvironment.

Figure 11:
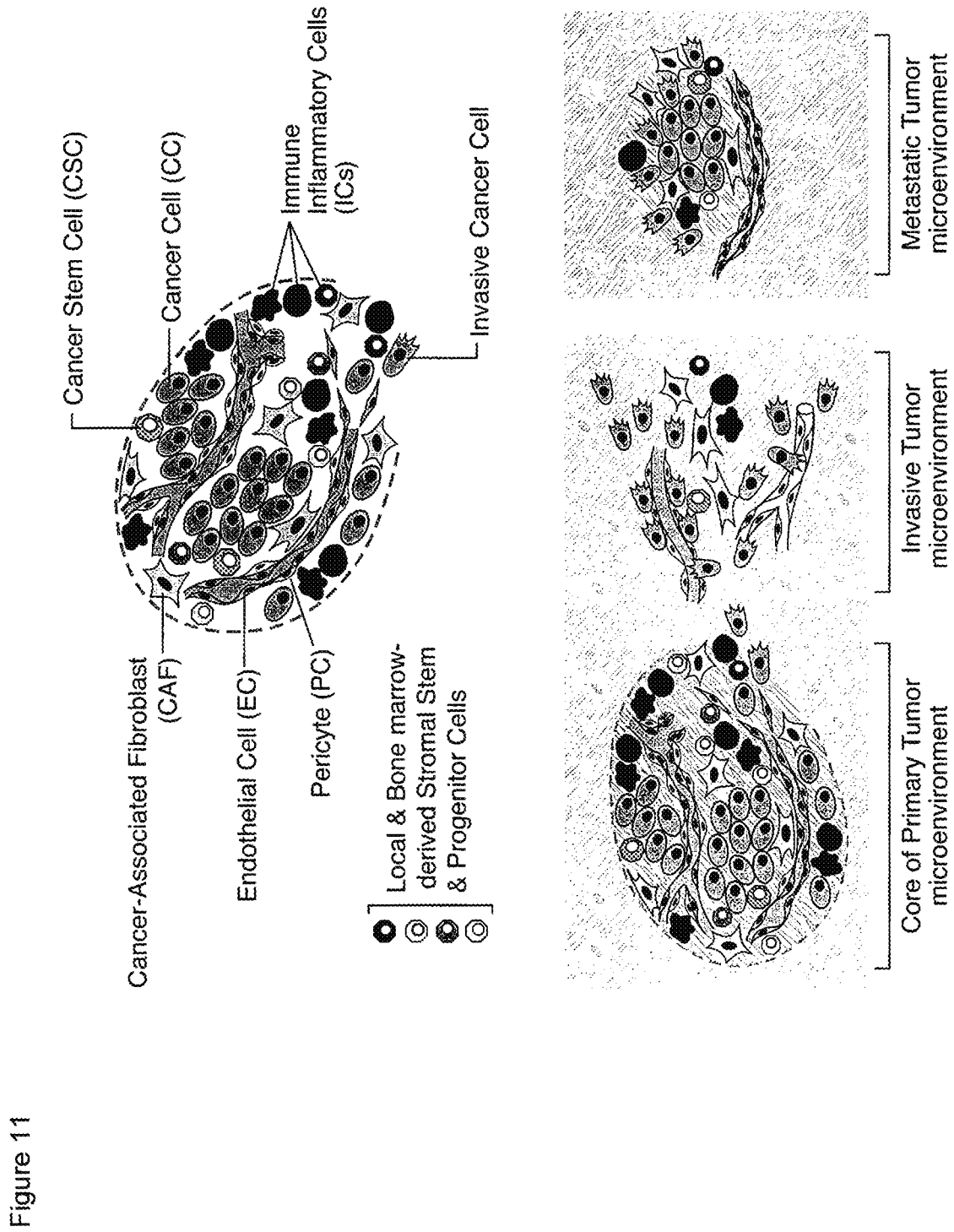
FIG. 11 shows the cells of the tumor microenvironment (Cell 144, Mar. 4, 2011, 646-674).

Tumors increasingly have been recognized as organs whose complexity approaches and may even exceed that of normal healthy tissues. Hanahan, D. and Weinberg, R. A., *Hallmarks of Cancer: The next generation*, Cell 144: 646-74 (2011). The biology of a tumor can be understood by studying the individual specialized cells within it (FIG. 11, upper), as well as the tumor microenvironment that they construct during the course of multistep tumorigenesis (FIG. 11, lower). Id.

As shown in FIG. 11, upper, an assemblage of distinct cell types constitutes most solid tumors. Both the parenchyma (functional tissue component) and stroma (connective tissue and supporting component) of tumors contain distinct cell types and subtypes that collectively enable tumor growth and progression. Id. Cancer cells initiate tumors and drive tumor progression forward. Traditionally, cancer cells within tumors have been portrayed as reasonably homogenous cell populations until relatively late in the course of tumor progression, when hyperproliferation combined with increased genetic instability spawn distinct clonal subpopulations. Reflecting such clonal heterogeneity, many human tumors are histopathologically diverse, containing regions demarcated by various degrees of differentiation, proliferation, vascularity, inflammation and/or invasiveness. Cancer stem cells within tumors impose a further dimension of intratumor heterogeneity. Id. The significance of CSCs as a distinct phenotypic subclass of neoplastic cells remains a matter of debate. Id.

Much of the cellular heterogeneity within tumors is found in their stromal compartments. Tumor-associated stromal cells may be supplied to growing tumors by proliferation of preexisting stromal cells, by differentiation in situ of local stem/progenitor cells originating in the neighboring normal tissue, or via recruitment of bone marrow-derived stem/progenitor cells. A key source of tumor-associated stromal cells is the bone marrow. (Id. Citing Bergfeld and DeClerck 2010; Fang and Salven (2011), Giaccia & Schipani (2010); Patenaude et al (2010); Lamagna & Bergers (2006)).

In many cases, fibroblasts constitute the preponderant cell population of the tumor stroma. The term "cancer associated fibroblast) includes at least two distinct cell types: (1) cells with similarities to the fibroblasts that create the structureal foundation supporting most normal epithelial tissues; and (2) myofibroblasts, identifiable by their expression of α-smooth muscle actin (SMA).

Endothelial cells forming the tumor-associated vasculature are prominent among the stromal constituents. Id. The role of endothelial cells forming lymphatic vessels is however poorly understood. Id. Pericytes represent a specialized mesenchymal cell type related to smooth muscle cells with finger-like projections that wrap around the endothelial tubing of blood vessels. Pharmacological inhibition of signaling through the PDGF receptor expressed by tumor pericytes and bone marrow-derived pericyte progenitors results in reduced pericyte coverage of tumor vessels, which in turn destabilizes vascular integrity and function. (Id. Citing Pietras and Ostman (2010); Raza et al (2010); Gaengel et al (2009)).

Infiltrating cells of the immune system are also constituents of tumors. Immune inflammatory cells present in tumors can include both tumor-promoting and tumor-killing subclasses. Id.

Infiltrating cells of the immune system are also constituents of tumors. Immune inflammatory cells present in tumors can include both tumor-promoting and tumor-killing subclasses. Id.

As shown in FIG. 11 (lower), the multiple stromal cell types create a succession of tumor microenvironments that change as tumors invade normal tissue and thereafter seed and colonize distant tissues. The abundance, histologic organization, and phenotypic characteristics of the stromal cell types, and of the extracellular matrix (hatched background), evolve during progression, thereby enabling primary, invasive, and then metastatic growth. The surrounding normal cells of the primary and metastatic sites, shown schematically, likely also affect the character of the various neoplastic microenvironments. Id.

According to one embodiment, the described invention provides a method for detecting, diagnosing and treating early stage (I/II) ovarian cancer in a subject comprising: (a) obtaining a serum sample from the subject and obtaining a normal serum control sample; (b) isolating from the sample obtained in (a) total RNA comprising a serine protease mRNA; (c) transforming the isolated total RNA of (b) into cDNA comprising serine protease cDNA; (d) amplifying the cDNA of (c); (e) measuring a level of amplified serine protease cDNA in (d) as a measure of expression of amplified serine protease mRNA; (f) comparing the level of expression of the amplified serine protease mRNA in (e) expressed by the subject with the level of expression of the amplified serine protease mRNA in (e) expressed by the normal serum control sample, wherein an increased level of expression of the serine protease mRNA expressed by the subject compared to the level of expression of the serine protease mRNA expressed by the normal serum control sample is indicative of possible early stage ovarian cancer in the subject; (g) when (f) is indicative of early stage (I/II) ovarian cancer in the subject, obtaining an ovarian tissue sample from subject; (h) isolating from the ovarian tissue sample obtained in (g) total RNA comprising serine protease mRNA; (i) transforming the isolated total RNA of (h) into cDNA comprising serine protease cDNA; (j) amplifying the cDNA of (i); (k) measuring a level of amplified serine protease cDNA in (j) as a measure of expression of amplified serine protease mRNA; (l) comparing the level of expression of the amplified serine protease mRNA in (k) expressed by the subject with the level of expression of the amplified serine protease mRNA in (k) expressed by a normal ovarian tissue control sample, wherein an increased level of expression of the serine protease mRNA expressed by the subject compared to the level of expression of the serine protease mRNA expressed by the normal ovarian tissue control sample is indicative of possible early stage ovarian cancer in the subject; (m) when both (f) and (l) are indicative of early stage ovarian cancer, diagnosing early stage (I/II) ovarian cancer in the subject; and (n) treating the subject with a treatment regimen effective to treat the early stage (I/II) ovarian cancer.

According to another embodiment, the described invention provides a method for detecting, diagnosing and treating early stage (I/II) ovarian cancer in a subject comprising: (a) obtaining a serum sample from the subject and a normal serum sample as a control; (b) detecting a serine protease protein in the samples from (a) by reacting an anti-serine protease antibody with the patient serum sample and the normal serum control sample; (c) quantifying an amount of serine protease protein bound by the anti-serine protease antibody in (b); (d) comparing the amount of serine protease protein in (c) bound by antibody in the subject serum sample with the amount of the serine protease protein bound by antibody in the normal serum control sample, wherein an increased amount of the serine protease protein bound in the subject sample compared to the amount of the serine protease protein bound in the normal serum control sample is indicative of early stage (I/II) ovarian cancer in the subject; (e) when (d) is indicative of ovarian cancer in the subject, obtaining an ovarian tissue sample from the subject and a normal ovarian tissue sample as a control; (f) detecting serine protease protein in the samples from (e) by reacting an anti-serine protease antibody with the subject ovarian tissue sample and the normal ovarian tissue sample; (g) quantifying an amount of serine protease protein bound by the anti-serine protease antibody in (f); (h) comparing the amount of serine protease protein bound in the subject ovarian tissue sample with the amount of the serine protease protein bound in the normal ovarian tissue control sample, wherein an increased amount of the serine protease protein bound in the subject ovarian tissue sample compared to the amount of the serine protease protein bound in the normal ovarian tissue control sample is indicative of early stage (I/II) ovarian cancer in the subject; (i) when both (d) and (h) are indicative of early stage ovarian cancer, diagnosing early stage (I/II) ovarian cancer in the subject; and (j) treating the subject with a treatment regimen effective to treat ovarian cancer.

According to one embodiment, the described invention utilizes serine proteases. Categories of serine proteases include, but are not limited to, trypsin-like, chymotrypsin-like and elastase-like. Non-limiting examples of trypsin-like serine proteases include trypsin, kallikrein (e.g., KLK6 and KLK7), PRSS8 (prostasin), granzyme K, hepatocyte growth factor activator and the like. Examples of chymotrypsin-like serine proteases include, but are not limited to, chymotrypsin, chymotrypsin-like protease-1 (CTRL-1), chymotrypsin-like neutral leukocyte protease and the like. Non-limiting examples of elastase-like serine proteases include neutrophil elastase (NE), proteinase 3 (PR3), azurocidin (AZU) and the like.

According to one embodiment, the serine protease is at least two (2) selected from the group consisting of kallikrein 6 (KLK6), kallikrein 7 (KLK7), and PRSS8

According to one embodiment, the described invention utilizes a sample obtained from a subject. The sample can include, but is not limited to, a tissue sample, a blood sample, a serum sample, a urine sample, a saliva sample and the like. Methods of obtaining a sample from a subject are well known in the art. Such methods include, but are not limited to, biopsy, such as for example, a core biopsy or a fine needle biopsy. The sample may be a fresh, a frozen or a fixed, wax-embedded sample. Non-limiting examples of fixed, wax-embedded samples include formalin-fixed, paraffin-embedded samples.

According to one embodiment, the described invention utilizes isolated nucleic acids. Nucleic acids include, for example, DNA, RNA and mRNA. Nucleic acids can be isolated, for example, from tissues, cells, blood, serum, plasma, urine, saliva, semen and the like. Protocols and reagents for isolating nucleic acids are known. Non-limiting examples of reagents used for nucleic acid isolation include guanidine thiocyanate, guanidine hydrochloride and guanidinium thiocyanate-phenol-chloroform; the proprietary formulation of this reagent is known as Trizol®.

According to one embodiment, the described invention utilizes methods employing amplification of nucleic acids. According to one such embodiment, amplification of nucleic acids is accomplished by Polymerase Chain Reaction (PCR). Non-limiting examples of PCR include conventional PCR, real-time PCR, quantitative PCR, quantitative real-time PCR, multiplex PCR, conventional reverse-transcriptase PCR (RT-PCR), real-time RT-PCR, quantitative RT-PCR, quantitative real-time RT-PCR, multiplex RT-PCR and the like.

Primers for PCR amplification of target sequences (e.g., mRNA sequences of KLK6 and KLK7 genes) can be designed based on the sequence of the target sequence, in accordance with standard procedures. Primers function to anneal and amplify a unique target sequence and as generators of a signal for detection and monitoring of an amplification reaction. According to some embodiments, the primers are unlabeled (such as in conventional PCR), while in other embodiments, the primers are labeled, such as with a fluorescent moiety. Labeled primers can be of any type, including those that are typically used in quantitative RT-PCR reactions, such as Scorpions, Molecular Beacons, and the like.

Probes may be provided in addition to primers. Probes that can be used for detection of amplification of the unique genomic sequences (e.g., TaqMan® probes) can be designed to hybridize to a sequence between the two amplification primers, preferably within 5-15 bases of one of the primer binding sites. Typically, probes are present in reaction mixtures in conjunction with primers or sets of primers for a particular amplification reaction, for example, an amplification of a unique target sequence. However, probes may be provided as separate components, which are separate from the primer(s) or other components of a reaction mixture.

The primers and probes are designed to have a typical size for primers and probes for use in PCR reactions. In general, the primers are relatively short (about 10-30 bases in length) oligonucleotides, while the probes (e.g., TaqMan® probes) may be from about 15-35 bases in length. The primers and probes are designed through a process that includes identification of unique sequences on a target nucleic acid, designing short oligonucleotides to amplify or detect those sequences, and synthesizing the oligonucleotides. Several characteristics may be taken into consideration when designing the primers and probe: e.g., the probe melting temperature should be higher than the primer melting temperatures, and the distance between the 3'-end of one primer and the 5'-end of the probe may be greater than 8 nucleotides. One of skill in the art may select among such considerations and characteristics to provide suitable primers and probes. Protocols for synthesis of oligonucleotides are known to those skilled in the art. Any suitable protocol may be used in synthesizing the primers and probes of the invention.

Quantitative real-time RT-PCR is an accurate, precise, high throughput assay. Real-time PCR automates the process of quantitating reaction products for each sample in every cycle. According to some embodiments, real-time PCR systems rely upon the detection and quantitation of a fluorescent reporter, the signal of which increases in direct proportion to the amount of PCR product in a reaction.

According to some such embodiments, for example, the reporter is the double-stranded DNA-specific dye SYBR® Green (Molecular Probes), which binds double-stranded DNA, and upon excitation emits light. Thus, as a PCR product accumulates, fluorescence increases. The SYBR® Green (Molecular Probes, Eugene, Oreg.) system is one way to detect and quantitate PCR products in real time. The SYBR® Green dye binds, in a sequence non-specific manner, to double-stranded nucleic acids. It thus can be used for detection and quantitation of double-stranded products produced from single-stranded templates (e.g., mRNA). Other detectable probes and primers, such as Amplifluor® probes, and DNAzymes, may be optimized to be used for quantitative detection of amplification products.

Alternatives to SYBR® Green include, but are not limited to, TaqMan (Applied Biosystems, Foster City, Calif.) and molecular beacons, both of which are hybridization probes relying on fluorescence resonance energy transfer (FRET) for quantitation. TaqMan® Probes are oligonucleotides that contain a fluorescent dye, typically on the 5' base, and a quenching dye, typically located on the 3' base. More specifically, for TaqMan® probes, when the probe is intact, the quencher quenches the signal produced by the fluorescent label. However, upon binding of the probe to the target sequence and subsequent digestion of the probe by the 5'-3' exonuclease activity of a polymerase, such as Taq polymerase, the fluorescent moiety is released from the quencher moiety, and a detectable signal, which is proportional to the amount of target nucleic acid being produced, is produced and can be monitored. According to one embodiment, Taq polymerase is used in qRT-PCR due to its 5'-3' exonuclease activity, and it changes the fluorescence of the probes and allows amplification of CDR1 mRNA. TaqMan® probes rely on degradation by a polymerase to generate a detectable signal, while Scorpions® and Molecular Beacons rely on opening of a hairpin structure to provide a detectable signal. Like TaqMan® probes, Scorpion® probes contain both a fluorescent moiety and quenching moiety on a single probe. However, unlike TaqMan® probes, Scorpions® are not degraded during the amplification reaction. Rather, they are designed as primers for amplification reactions. Scorpion® primers are designed to form hairpin structures in solution, which causes the fluorescent moiety and the quenching moiety to be in close proximity. Binding of the primers to target nucleic acids unfolds the hairpin structure and moves the quenching moiety a sufficient distance away from the fluorescent moiety that detectable fluorescence is emitted.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. When a molecular beacon hybridizes to a target, the fluorescent dye and quencher are separated, FRET does not occur, and the fluorescent dye emits light upon irradiation.

Multiplexing of PCR reactions is common. Multiplexing allows an investigator to assay two or more different gene targets in a single reaction through the use of multiple probes or primers, each specific for its own target and each comprising a fluorescent moiety that emits at a unique wavelength (as compared to the other probes). Multiplexing is possible with TaqMan® probes, Molecular Beacons, and Scorpions. Due to its non-specific binding nature, SYBR® Green may not be amenable to multiplexing.

Generally, a quantitative RT-PCR reaction is performed by one of two methods: comparison to a standard curve or comparison of Ct values. In the first of these methods, a standard curve of amplification products of a particular mRNA is made based on amplification of a series of different, known amounts of a pre-selected nucleic acid. Amplification results of reactions performed on a target nucleic acid are then compared to the standard curve to obtain a quantity, and that quantity can be extrapolated to an amount of the target in the original sample. While it is preferred to use an mRNA as the source for the standard curve, the stability of mRNA is known to affect the validity of such standard curves, and overcoming or minimizing this problem has proved to be difficult. To avoid the problems associated with using mRNA as a source for the standard curve, researchers have used DNA for generation of standard curves. While use of DNA overcomes the problems associated with use of mRNA, the mere fact that it avoids the problems creates yet another problem, i.e., because DNA templates are relatively stable, and because amplification of DNA does not require a first-strand synthesis step (which can be inefficient and variable across samples or preparations), the standard curves produced from DNA sources often do not correlate accurately to the amount of mRNA in a test sample.

In the Ct comparison method for quantitating PCR products, expression of a housekeeping gene (such as β-actin) is used as a standard against which amplification of a target nucleic acid (e.g., KLK6 and KLK7) is compared. Often, in this method, a comparison of expression of the target nucleic acid under two different conditions is performed to determine changes in expression patterns. This method avoids the problems associated with instability of RNA or use of DNA as a control that is seen when using the classical standard curve method.

Controls are amplified in the same PCR reaction mixture as the target sequence in an effort to quantitate PCR products and determine amounts of target nucleic acids in a sample. These controls are often transcripts of housekeeping genes. Such housekeeping genes include, but are not limited to, β-actin and GAPDH. The control is added to the reaction mix and co-amplified with the target nucleic acid. Fluorescent probes specific for both are included in the mixture, and two amplification curves are obtained. The relative expression of the target nucleic acid with respect to the control is then determined. Using this technique, multiple, different samples can be compared for expression of a target gene (e.g., KLK6 and KLK7), with reference back to the same control. Although adding a control to amplification reactions can be a useful alternative to other methods of quantitating expression levels, and can be a useful method for normalizing PCR reactions across samples, it does not allow one to determine absolute amounts of materials present in the amplification reaction mixture or in the original sample. Rather, the results are qualitative or semi-quantitative, giving an idea only of the amount of one nucleic acid (e.g., the target) in comparison to another (e.g., the control).

According to one embodiment, the described invention provides methods that detect a protein in a sample obtained from a subject. Such methods of protein detection are well known in the art and include, but are not limited to, Western blot, immunohistochemistry, enzyme-linked immunosorbant assay (ELISA), radioimmunoassay and the like.

Methods that detect proteins may employ antibodies. Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, chains comprise but a few percent of the total; in the dog and cat, κ chains are very low; the horse does not appear to have any K chain; rabbits may have κ to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens.

The term "antibodies" can include, for example, polyclonal antibodies, monoclonal antibodies, antibody fragments and the like.

For example, monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

For example, diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

For example, the technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

According to one embodiment, the ovarian cancer is selected from the group consisting of serous, papillary serous, metastatic, borderline, mucinous and clear cell.

According to one embodiment, the described invention provides the detection of low-grade (e.g., G1) ovarian cancer. Methods for grading of tumors are well-known. For example, tumor grade can be determined by microscopic examination of cancer tissue. Low-grade ovarian cancer can be characterized by well-differentiated tissue, low-grade nuclei with infrequent mitotic figures and the like.

According to one embodiment, the described invention provides the detection of stage I (e.g., IA, IB, IC1, IC2 and IC3)) ovarian cancer. Staging of tumors is well-known in the art. For example, tumor stage can be determined by tests including, but not limited to, ultrasound, computerized tomography (CT) scan, positron emission tomography (PET) scan, magnetic resonance imaging (MRI), X-ray and biopsy. Stage I ovarian cancer can be characterized by a tumor limited to one ovary, capsule intact, no tumor on ovarian surface and negative washing; a tumor involving both ovaries, capsule intact, no tumor on ovarian surface and negative washings; surgical spill; capsule rupture before surgery or tumor on ovarian surface; malignant cells in ascites or peritoneal washings and the like.

According to one embodiment, an increased level of expression of two or more of KLK6 mRNA, KLK7 mRNA, and PRSS8 mRNA expressed in ovarian tissue of a subject compared to the level of expression of two or more of KLK6 mRNA, KLK7 mRNA, and PRSS8 mRNA expressed by a normal ovarian tissue control sample is indicative of an expansion of tumor epithelial compartment cells.

According to one embodiment, an increased level of expression of two or more of KLK6 protein, KLK7 protein, and PRSS8 protein expressed in ovarian tissue of a subject compared to the level of expression of two or more of KLK6 protein, KLK7 protein, and PRSS8 protein expressed by a normal ovarian tissue control sample is indicative of an expansion of tumor epithelial compartment cells.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range.

Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods
Bioinformatics

The Biomax BioXM™ Knowledge Management System (Biomax Informatics AG, Munich, Germany) was used to mine and generate a rank list of candidate ovarian cancer genes from the 6,955 manually curated cancer genes and 2,200 biomarker genes of the National Cancer Institute (NCI) and the Cancer Gene Index (CGI). The Biomax BioLT™ Tool (NLP) was used to mine 18 million Medline abstracts (94 million sentences) and 24,000 Hugo genes to find and validate genes associated with cancer terms, gene-disease relationships, and gene-compound/treatment relationships for each of the 6,955 cancer genes. The NCI Thesaurus Role Codes and Karp's Evidence Codes (Karp, S. et al., Pacific Symposium on Biocomputing 9: 190-201 (2004)) were used to annotate over 1.3 million related sentences. The search for potential biomarkers was performed by initiating queries on BioXM with a combination of search terms, including ovarian, cancer, biomarker, overexpression, and upregulation or downregulation.

Cell Lines and Cell Culture

Ovarian cancer cell lines TOV21G, TOV112D, OV-90, CAOV3, SKOV3, PA-1, SW626, and ES-2 were purchased from the American Type Culture Collection (ATCC, Manassas, Va.) and cultured in the media suggested by the distributor. The SKOV-1, IGROV-1, HEY, OV-2008, A2780, UCI-101, and UCI-107 cells were obtained from Drs. Howell (University of California, San Diego) and Carpenter (University of California, Irvine), and all were cultured in RPMI 1640 medium (Invitrogen, Carlsbad, Calif.). The DOV13 cell line was obtained from Dr. Bast (MD Anderson Cancer Center) and cultured in DMEM. The CSOC882 cells were obtained from Dr. Karlan (University of California, Los Angeles) and cultured in McCoy's 5A medium. Cell line 2774 was obtained from Dr. Wolf (MD Anderson Cancer Center) and cultured in EMEM. The BG-1 cell line was obtained from Dr. Korach (NIEHS, National Institutes of Health) and cultured in a 1:1 mixture of DMEM and F12 media without phenol red. The normal ovarian epithelial cell lines FHIOSE118 and IOSE523 were obtained from Dr. Cheng (Moffitt Cancer Center) and Dr. Nelly Auersperg (University of British Columbia), respectively, and cultured in a 1:1 mixture of MCDB 105 and Medium 199. All culture media were supplemented with 5-15% v/v fetal bovine serum (FBS; Hyclone, Logan, Utah) and penicillin/streptomycin solution (Invitrogen).

RT-PCR and Statistical Analysis

Total RNA was extracted from cells using Trizol (Invitrogen), and cDNA was generated with the SuperScript III RTS First-Strand cDNA Synthesis Kit (Invitrogen) as described by the manufacturer. All amplification primers were synthesized for use with the ABI7900 RT-PCR device (Applied Biosystems, Foster City, Calif.) as recommended by Applied Biosystems, and they were demonstrated to produce a single PCR band of the expected size by electrophoresis through agarose gels of end-point PCR from cDNA template generated from normal ovarian cell lines. Typically, the primers were 20mers with melting temperatures (Tm) of 58° C. For qPCR, 43 ng of cDNA, 10 pmole primers and SYBR Green PCR Master Mix (Applied Biosystems) was used in a 20 µl total volume. All qPCR assays used MicroAmp Fast Optical 96-Well Reaction Plates with Barcode (Applied Biosystems) in the standard mode (first denaturation at 95° C. for 10 minutes, and then 40 cycles at 95° C. for 15 seconds followed by 60° C. for 1 minute). The qPCR data were normalized against internal GAPDH or f3-actin cDNA and then analyzed by software provided with the ABI7900. Poor quality specimens that produced no meaningful values after 40 cycles of qPCR were not included in the data processing steps. The TissueScan Cancer Survey Panel was used for screening 22 different human cancer types (over 380 biospecimens) and the Ovarian Cancer Panel I-IV was used for determining the expression level of genes at various stages, grades and subtypes of ovarian cancer (over 190 biospecimens) (both from OriGene, Rockville, Md.) as described by the manufacturer. Tissue Scan Survey Panels were purchased in a 96-well format with lyophilized cDNA from various patients with different cancer types. Each well of the plate contained 2-3 ng of cDNA and the plate was divided to scan two genes. The reaction mix was transferred to a 'Fast Plate', which is compatible with the ABI 7900 HT RT-PCR machine. After dividing each plate into two 'Fast-Plate', each reaction consisted of approximately 1-1.5 ng of cDNA. The conditions used are as follow: $1^{st}$ denaturation at 95° C. for 10 minutes followed by 40 cycles of 95° C. for 15 seconds and 60° C. for 1 minute. The data from Tissue Scan panels was normalized using beta-Actin. All cancer tissues in these panels contain an average of 75% cancer cells and 25% surrounding stroma. Ovarian tissue samples were also obtained from tissue banks at the MD Anderson Cancer Center (MDACC) and Thomas Jefferson University (TJU), both IRB-approved. All qRT-PCR assays were done in duplicate, and experiments were repeated a minimum of two times. For statistical analysis, SigmaPlot 12 (SysStat Software, Chicago, Ill.) or JMP4 (SAS Institute) software was used to determine p values of differences in expression between ovarian and other cancer types versus corresponding normal tissues. A t-test or analysis of variance (ANOVA) was used to calculate differences between means of sample groups versus normal controls and derive the corresponding p values.

Immunohistochemistry

Whole-mount paraffin-embedded tissues and tissue arrays (US Biomax, Rockville, Md.; Proteogenex, Culver City, Calif.; and the Tissue Bank of Thomas Jefferson University, IRB-approved) were subjected to histochemical staining as described by the manufacturers of antibodies. Tissue sections were de-paraffinized using Histochoice clearing agent (Amresco, Solon, Ohio) for 5 minutes followed by hydration steps with 100%, 90%, 70% and 50% ethanol for 5 minutes each. After equilibrating with PBS for 5 minutes, the tissues were incubated with high pH solution (Amresco) at 95° C. for 20 minutes to retrieve antigens. Sections were cooled and washed with PBS for 5 minutes, endogenous peroxidases were blocked by incubating in 30% $H_2O_2$ for 15 minutes, sections were marked with hydrophobic PAP pen (Vector Labs, Burlingame, Calif.), blocked for 3 hours with 5% BSA in PBS/0.1% Tween-20, and then incubated in primary antibodies overnight at 4° C. The sections were washed twice in PBS/0.1% Tween-20 for 10 minutes each and then once in PBS for 10 minutes. The tissues were incubated with appropriate secondary antibody (Jackson ImmunoResearch Laboratories) for 2 hours followed by the same washing steps described above. Diaminobenzidine (DAB) kit (Vector Labs) was used to visualize the antigen; color development was interrupted by washing with distilled water for 5 minutes. Hematoxylin (Amresco) was used as the counterstain to visualize the nuclei. The sections were dehydrated by using ethanol solutions in the sequence of 50%, 70%, 90%, 100% for 5 minutes each and 5 minutes in Histochoice clearing agent. Diaminobenzidine (DAB) staining was visualized by brightfield microscopy. After mounting the tissues (Permount, Vector Labs), the slides were photographed with an Axio Imager Microscope (Carl Zeiss, Thornwood, N.Y.), and images were taken at 20× and 40× magnification.

In Situ Hybridization

Ovarian tissue sections were deparaffinized, processed for high-pH antigen retrieval, deproteinated by proteinase K treatment (10 μg/ml) (Roche) in a 37° C. water bath for 20 minutes and then treated with 0.2% w/v glycine for 30 seconds to inactivate the enzyme. After fixing the sections with 4% w/v paraformaldehyde (PFA; Electron Microscopy Sciences, Fort Washington, Pa.) for 10 minutes, the sections were blocked with hybridization buffer (50% v/v formamide, 5× saline-sodium citrate (SSC), 9.2 mM citric acid, 50 μg/ml heparin, 500 μg/ml yeast RNA, and 0.1% v/v Tween-20) for 2 hours at 54° C. The sections were incubated overnight in a humidified chamber with digoxigenin (DIG)-labeled probes (20 nM, Exiqon, Woburn, Mass.). The sequence of the KLK6 probe was 5'-DIG-GACCAAGTC-CTCACTCATCAC-3' (SEQ ID NO: 1), and for the KLK7 probe was 5'-DIG-AAAGTACACAGAAGGAAGGAGA-3' (SEQ ID NO: 2). The sequence of the PRSS8 probe was 5'-DIGN-GCAGTAAAACTCCTGACTCTCA (SEQ ID NO: 3). The sections were washed for 30 minutes three times with hybridization washing solution (50% v/v formamide containing 2×SSC) at 54° C. and then with washing solution (0.1% v/v Tween-20 in phosphate-buffered saline, PBS) for 5 minutes five times at room temperature. After blocking for 3 hours at room temperature with 5% w/v bovine serum albumin (BSA), the sections were treated with mouse anti-DIG antibody (SC-57583, Santa Cruz Biotechnology, Santa Cruz, Calif.,) at a dilution of 1:1000 in 5% BSA overnight. The sections were washed in PBS containing 0.1% v/v Tween-20 for 5 minutes four times, and then once in PBS for 5 minutes. To visualize bound probe, the Envision G/2 System/AP Rabbit/Mouse Permanent Red kit (Dako, Carpinteria, Calif.) was used as described by the manufacturer. The stained tissues were further processed and photographed as described above for immunohistochemistry.

Immunoblot Analysis

Serum samples from ovarian cancer patients (n=44) and normal female donors (n=10) were purchased from Proteogenex (Costa Mesa, Calif.) and Bioserve (Beltsville, Md.); these samples represent diverse tumor stages, age groups, and races. The abundant serum proteins were depleted with ProteoPrep Blue Albumin and IgG Depletion Kit (both from Sigma-Aldrich, St. Louis, Mo.) as described by the manufacturer prior to separation of samples by electrophoresis through sodium dodecyl sulfate-containing polyacrylamide gels (SDS-PAGE). The columns were equilibrated using the equilibration buffer provided with the kit. Serum sample (65 μl) was added and incubated at room temperature for 10 minutes to the equilibrated column containing medium bed, and the column was then centrifuged for 60 seconds at 12,000 rpm and the eluate was reapplied to the medium bed, incubated for 10 minutes and spun as before, followed by washing the column with equilibration buffer (100 μl), and then pooling with the depleted serum. Bradford Assay (Bio-Rad Laboratory, Hercules, Calif.) was used to measure the protein concentration. Twenty micrograms (20 μg) of proteins from eluates in loading buffer (0.5 M Tris-HCl, 0.15 M NaCl, 1% IGEPAL, mini complete (Roche Applied Science, Indianapolis, Ind.) containing 10 μg/ml leupeptin, 10 μg/ml aprotinin, 1 mM p-methylsulfonylfluoride (PMSF), 1 mM NaVO3, 0.05 M NaF, and 1 mM EGTA) were resolved by SDS-PAGE in 12.5% w/v gels, transferred to nitrocellulose membranes (Bio-Rad Laboratory) and then further examined by Western blot analysis. The membranes were probed with primary anti-KLK6 antibody, (H60) primary anti-KLK7 (1407) antibody and primary anti-PRSS8 antibody (Santa Cruz Biotechnology) and then with appropriate horseradish peroxidase (HRP)-conjugated secondary antibodies (Jackson ImmunoResearch Laboratories, West Grove, Pa.). The reactive proteins were visualized by chemiluminescence with SuperSignal West Dura substrate (Thermo Fisher Scientific, Rockford, Ill.).

Enzyme-Linked Immuno-Sorbent Assay (ELISA)

ELISA kits (R&D Systems, Minneapolis, Minn.) for measuring production of CA-125 and HE4 from corresponding ovarian cancer patients' serum (Proteogenix, Culver City, Calif.) were used for this study and the manufacturer's protocol was followed. Briefly, all reagents, standard dilutions and samples were prepared as directed in the product insert. Next, excess microplate strips from the plate frame were removed and returned to the foil pouch containing desiccant and resealed. 100 μL of Assay Diluent was added to each well. Next, 100 μL of Standard, control, or sample was added to each well, the wells were covered with a plate sealer, and the wells were incubated at room temperature for 2 hours on a horizontal orbital microplate shaker. After incubation, the wells were aspirated and washed 4 times according to the product insert. Next, 200 µL of Conjugate was added to each well, the wells were covered with a new plate sealer, and the wells were incubated for 2 hours at room temperature on a horizontal orbital microplate shaker. Following incubation, the wells were aspirated and washed 4 times according to the product insert. 200 µL of Substrate consisting of 19 ovarian cancer cell lines and normalized against IOSE523. Out of the 33 genes, thirteen (13) genes showed robust differential expression in the majority of the 22 ovarian cancer cell lines versus normal ovarian cell lines examined (p<0.05). These 13 genes were selected to be screened against the Tissue Scan Panels containing cDNA from 18 different cancer types. Of the 13 genes screened, 3 genes (KLK6, KLK7 and PRSS8) were over expressed only in ovarian cancer.

TABLE 3

Bioinformatic-based data mining method for the identification of potential ovarian cancer biomarkers.
Potential biomarkers for ovarian cancer

| ATP7B | Ca125 | CLEC3B | KLK6 | TOP2A | ARID4B | CEA | ID2 | IGFBP2 | INHA |
|---|---|---|---|---|---|---|---|---|---|
| PDGFA | HE4 | DUSP1 | BSG | CLDN3 | REEP5 | MIF | IGF2BP1 | LGALS3BP | CDC25C |
| BRCA2 | CA72-4 | IL13RA2 | STAT3 | CLDN4 | CCT3 | AFP | IQGAP1 | MSLN | NME1 |
| DNAJC15 | BARD1 | PLK1 | RAET1E | COPS5 | CD47 | Prolactin | RHOC | ST14 | AKT2 |
| KLK14 | BCL2 | VIL2 | TITF1 | CSF1 | ETV4 | MUC 1 | RNASE2 | Amh | ANGPT2 |
|  |  |  |  |  |  |  | AMH |  |  |
| KLK9 | IGFII | APOD | TFF1 | EFNB1 | MAGEA4 | AMH | SYCP1 | CDC25A | XIST |
| WFDC2 | BAG1 | CD247 | SPINK1 | KLK11 | SCGB2A1 | WT1 | TRIM25 | CSF1R | KLK10 |
| ERCC1 | BAG3 | CDC25B | PRSS8 | KLK13 | SIX5 | OGP | P11 | GADD45A | KLK15 |
| KLK8 | BAG4 | DAB2 | CCNE1 | MVP | ZNF217 | CDX2 | CYP2A | HLA-G | KLK5 |
| RBL2 | Osteopontin | HMGA1 | CEACAM6 | PARP1 | EYA2 | SMRP | PTK2 | JUP | KLK7 |
| SKP2 | Maspin | HOXB7 | ETS1 | VEGFC | ELF1 | Bcl-xL | TACC3 | MLANA | SOD1 |
| IGFBP5 | MSN | BCHE | EPHA2 | ASNS | MUC5AC | TNFRSF1B |  |  |  |

Solution was added to each well and incubated for 30 minutes at room temperature on the benchtop protected from light. After incubation, 50 µL of Stop Solution was added to each well. Each well was read at 450 nm (with wavelength correction set to 540 nm or 570 nm) within 30 minutes.

Recombinant human CA-125 (R&D Systems, Minneapolis, Minn.) or HE4 (Novoprotein, Summit, N.J.) were used as positive controls and were further diluted as standards. Nineteen (19) serum samples of early stage patients (stage I, 7 patients; and stage II, 12 patients) were evaluated for this purpose. CA-125 and HE4 proteins were compared in two stage III and two stage IV patients. Levels of these proteins also were measured in serum of three normal individuals. Serum was diluted (1:4) before measurements and results were calculated as averages of triplicates of each serum sample. The colorimetric results were read at 495 nm on a BioTek Synergy HT reader. Gene5 software was used to read and analyze the results.

Example 1: Pre-Screening of Potential Ovarian Cancer Biomarkers Using Bioinformatics To pre-screen human genes with high potential for use as early detection biomarkers, the BioXM bioinformatics platform was used with query strings including ovarian, biomarker, upregulation, downregulation, and overexpression, to mine and generate a rank list of candidate ovarian cancer genes from the 6,955 manually curated cancer genes of the National Cancer Institute (NCI) Cancer Gene Index (CGI). This cancer gene database was originally derived from clinicopathology-based projects (e.g., tumor staging) and is generally accepted to be a source of clinically relevant biomarkers for diagnostic use, especially for early cancer detection. The output data set contained a qualified list of 125 genes that represent diverse processes, including apoptosis, proliferation, invasion, metabolism, and angiogenesis. Genes were characterized based on signaling pathways. From the 125 genes, 33 genes were either over- or under-expressed. These 33 genes were validated using a library Example 2: Pre-screening of Potential Ovarian Cancer Biomarkers Using a Library of Ovarian Cancer Cell Lines Expression pre-screening in ovarian cancer cell lines is a practical solution for obtaining broad expression profiles while sparing invaluable patient samples. In this study, a library of 19 ovarian cancer and two normal ovarian cell lines was used for mRNA expression screening. The phenotype of normal ovarian cell lines was a mixture of epithelial and fibroblastic (data not shown). Initially, all 117 genes were tested against seven ovarian cancer cell lines representing different grades and subtypes and against two normal ovarian cell lines by qRT-PCR.

As seen in FIG. 1A, mRNAs of the clinically established ovarian cancer biomarkers CA125 (cancer antigen 125), HE4 (human epididymis protein 4), and CEA (carcinoembryonic antigen) were overexpressed in all these lines. From the first stage of screening, 30 candidate genes were selected that were differentially expressed in cancer versus control cell lines: APOD (apolipoprotein D), BCHE (butyrylcholinesterase), BCL-2 (B-cell lymphoma 2), CA125, CDX2 (caudal type homeobox 2), CLDN3 (claudin 3), CLDN4 (claudin 4), CSF1(colony stimulating factor 1), DAB2 (mitogen-responsive phosphoprotein, homolog 2), DUSP1 (dual specificity phosphatase 1), ETS1 (v-ets avian erythroblastosis virus E26 oncogene homolog 1), IGFBP5 (insulin-like growth factor binding protein 5), IL13RA2 (interleukin 13 receptor, alpha 2), JUP (junction plakoglobin), KLK5 (kallikrein 5), KLK6 (kallikrein 6), KLK7 (kallikrein 7), KLK8 (kallikrein 8), KLK13 (kallikrein 13), MAGEA4 (melanoma antigen family A, 4), MASPIN (mammary serpin), MIF (macrophage migration inhibitory factor), MLANA (melan-A), MSLN (mesothelin), P11 (S100 calcium binding protein A10), PRSS8 (protease serine 8), ST14 (suppression of tumorigenicity 14), TNFRSF1B (tumor necrosis factor receptor superfamily member 1B), VEGFC (vascular endothelial growth factor C) and WFDC2 (HE4; Human Epididymis Protein 4). Of these, 12 genes were consistently either up- or downregulated more than 10-fold in more than 70% of all ovarian cancer cell lines that represent different grades derived from mostly late-stage ovarian cancer: BCL2, CDX2, KLK7, KLK6, P11 and PRSS8 genes were upregulated, and IGFBP5, DUSP1, DAB2, VEGFC, IL13RA2, and APOD genes were downregulated. Among these 12 genes, KLK6 and KLK7 were consistently upregulated (>10-fold) in the majority of the ovarian cancer cell lines originally created for mRNA expression screening (FIG. 1B).

Example 3: Elevated Expression of KLK6 and KLK7 mRNA in Ovarian Cancer Specimens In this study, expression of the selected 12 genes was analyzed by qRT-PCR as a final screening step, measured in normal and cancer samples from 394 individuals and representing 18 different tumor types, apart from ovarian cancer.

Figure 2:
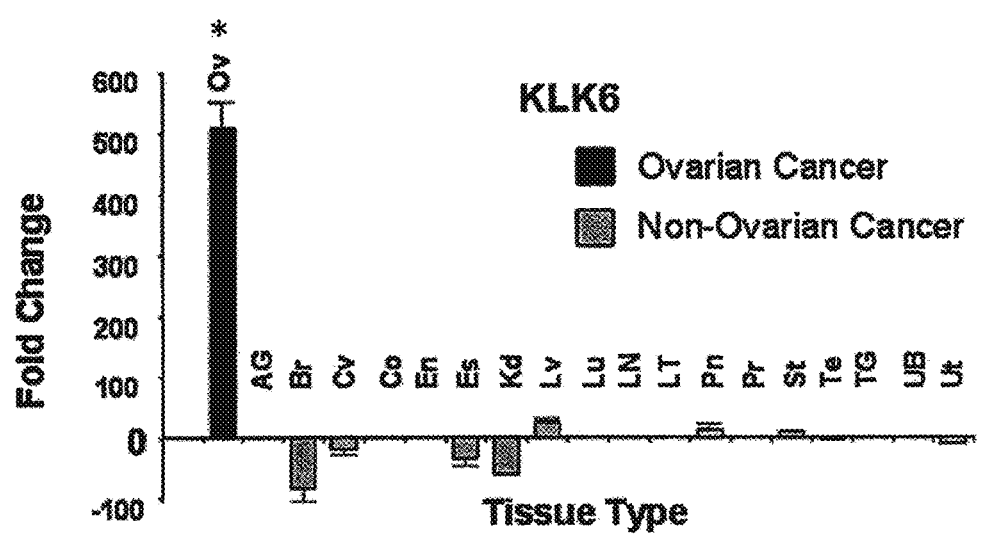
FIG. 2 shows differential expression of KLK6 and KLK7 genes is significantly selective for ovarian cancer versus 18 other human cancer types. Over 390 cDNAs derived from 19 different cancer tissues and corresponding normal tissues were assayed by RT-qPCR to quantitatively measure KLK6 (A) and KLK7 (B) gene expression. The fold change represents the level of gene expression in cancer normalized against the corresponding normal tissue. The mean number of samples used in the assay was 15 for cancer and five for corresponding normal tissues. The statistical significance of differential KLK6 and KLK7 expression in ovarian cancer (solid black bar) over other cancer types (solid gray bars) was determined to be $p<0.005$ by one-way ANOVA (SigmaStat). Abbreviations for cancer types are Ov=ovarian, AG=Adrenal Gland, Br=Breast, CV=Cervix, Co=Colon, En=Endometrium of Uterus, Kd=Kidney, Es=Esophagus, Lv=Liver, Lu=Lung, LN=Lymph Node, LT=Lymphoid Tissue, Pn=Pancreas, Pr=Prostate, St=Stomach, Te=Testis, TG=Thyroid Gland, UB=Urinary Bladder, and Ut=Uterus.
Figure 2:
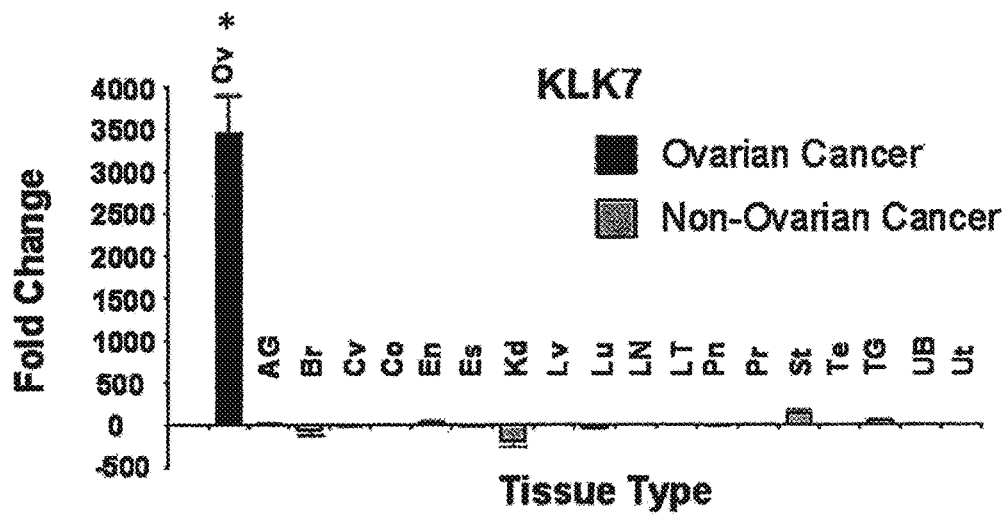

The analysis indicated that the mean differential mRNA expression between ovarian tumor versus normal ovarian tissues was over 500-fold for KLK6 ($p<0.001$) and over 3000-fold for KLK7 ($p<0.001$). The normal control was a mixture of epithelial and stromal components, representing the true normal ovary. In addition, the differential overexpression of both mRNAs was highly specific to ovarian cancer relative to "cancer versus corresponding normal tissues" of other cancer types ($p<0.001$ at 95% confidence level, CI=20 with 30% of total population) (FIG. 2). The difference between cancer versus corresponding normal tissue was greatest in ovarian cancer compared with other major cancer types. The expression of KLK6 and KLK7 was downregulated in breast (87-fold and 75-fold, respectively) and kidney cancers (68-fold and 234-fold, respectively) relative to corresponding normal tissues.

Without being bound by theory, the higher expression of KLK6 and KLK7 genes in ovarian carcinomas versus normal ovarian tissues (largely stroma elements; >100-fold difference) suggests that basal expression may be tightly regulated in the epithelium by the presence of hormones and other factors in normal ovaries.

Example 4: Expression of KLK6 and KLK7 mRNAs in Subtypes, Grades and Stages of Ovarian Cancer In this study, the gene expression patterns of KLK6 and KLK7 in ovarian cancers were analyzed by qRT-PCR in 192 cDNA samples derived from normal (n=27) and ovarian cancer (n=135 and 142 for KLK6 and KLK7, respectively) tissues representing eight major subtypes of epithelial origin, including papillary serous, serous, endometrioid, mucinous, clear cell, metastatic carcinoma, and borderline cases.

Figure 3:
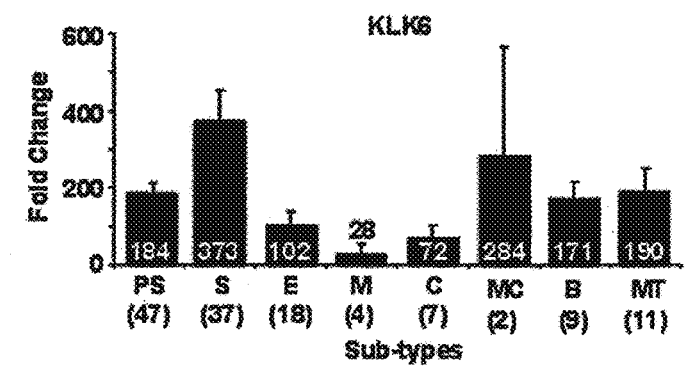
FIG. 3 shows expression of KLK6 and KLK7 genes is subtype-specific (A) and increases progressively in advanced stages (B) and higher grades (C) of ovarian tumors. Gene expression levels quantitatively measured by qRT-PCR in cDNAs derived from ovarian tumors versus normal ovarian tissue. The level of fold change is represented by the height of each histogram, and error bars are indicated. Abbreviations for ovarian cancer subtypes in (A) are PS=Papillary Serous, S=Serous, E=Endometrioid, M=Mucinous, C=Clear Cell, MC=Metastatic Carcinoma, B=Borderline and MT=Mixed Type. Abbreviations used in (B) are G1, G2, and G3, which represent progressive tumor grades; GB is the grade corresponding to borderline subtypes. In (C), the four progressive tumors stages are denoted as I, II, III, and IV. The number of ovarian tumor samples analyzed is given in parentheses.
Figure 3:
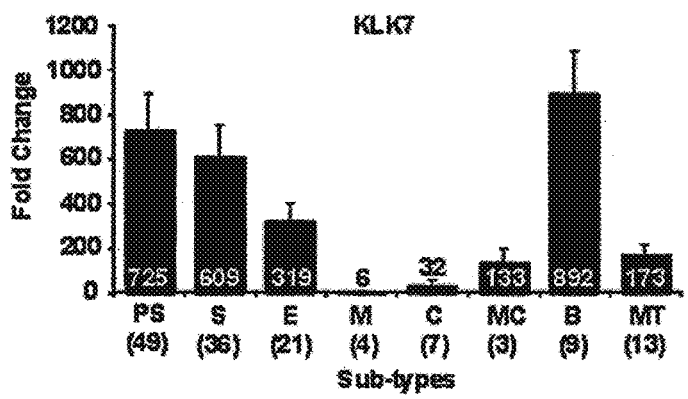
Figure 3:
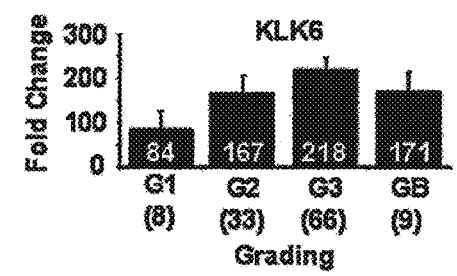
Figure 3:
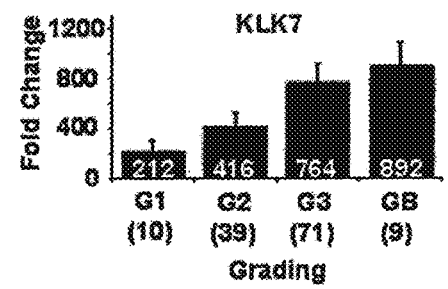
Figure 3:
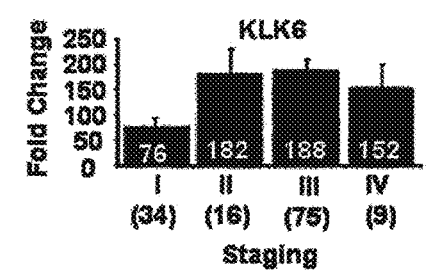
Figure 3:
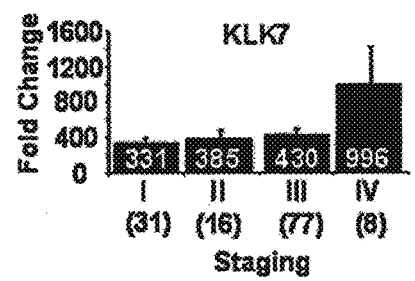

First, subtype-dependent expression of KLKs was evaluated. Both KLK6 and KLK7 mRNAs were significantly overexpressed ($p<0.005$) in papillary serous, serous, metastatic carcinoma, borderline carcinomas and mixed-type carcinomas versus normal ovary tissues (FIG. 3A). Both genes were also overexpressed ($p<0.01$), albeit to a lesser extent, in mucinous and clear cell subtypes, especially for KLK6. This overexpression signature was found in subtypes that occur in more than 90% of ovarian cancers. Thus, KLK6 and KLK7 are potential candidates for early detection markers.

Next, grade-dependent expression was evaluated and it was found that KLK6 and KLK7 transcripts were overexpressed 84- and 212-fold, respectively, in low-grade (G1) tumors versus normal controls ($p<0.001$). Expression of both KLK 6 and KLK 7 increased >3-fold from lower (G1) to higher (G3) tumor grades or to borderline (GB) tumors (FIG. 3B).

For tumor staging, both KLK6 and KLK7 mRNA levels were elevated 76-fold and 331-fold, respectively, in stage I versus the normal controls ($p<0.001$) (FIG. 3C). The expression of KLK6 and KLK7 was not statistically significant ($p>0.05$) between subsequent grades and stages. The elevated mRNA levels were maintained in advanced tumor grades and stages.

Together, these data suggest that KLK6 and KLK7 can be useful as biomarkers for detection of low-grade and early stage ovarian cancers.

Example 5: Overexpression and Specificity of KLK6 and KLK7 in Tumor Epithelia

In this study, the overexpression and localization of KLK6 and KLK7 were verified by histologic analysis of 512 samples of normal ovary and ovarian tumors and by hybridization of customized oligonucleotide probes for each gene in situ on either whole mount or tissue arrays.

Figure 4:
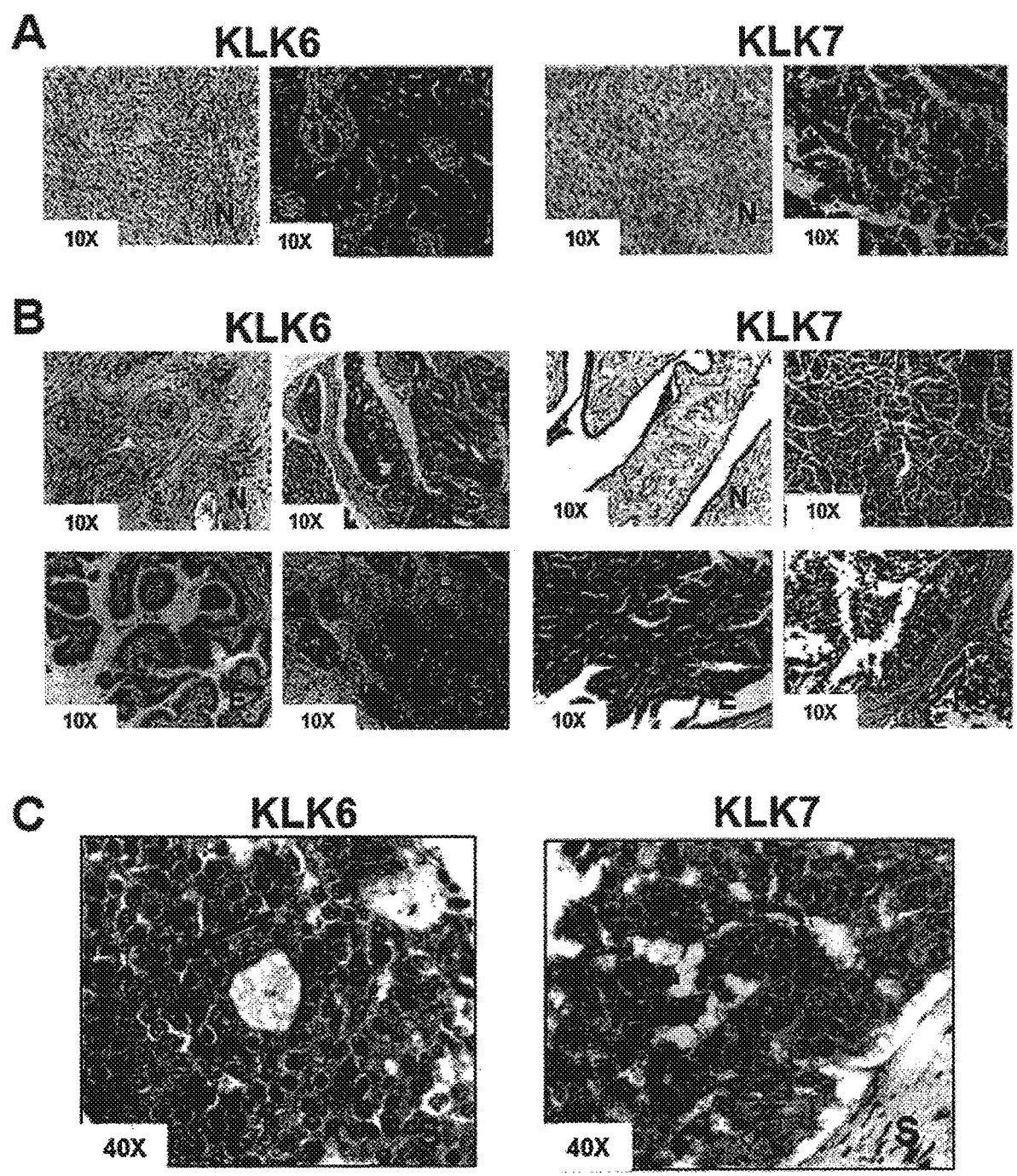
FIG. 4 shows KLK6 and KLK7 genes and proteins are overexpressed in epithelia but absent in stroma of ovarian tumors. (A) To detect mRNA in tissues, serous ovarian tumors (S) and normal tissues (N) were hybridized in situ with KLK6 and KLK7 oligonucleotide probes followed by visualization of red chromogen staining by brightfield microscopy under 10× magnifications. (B) To detect KLK6 and KLK7 protein expressions in tissues, subtypes of ovarian tumors (S=Serous, PS=Papillary Serous, E=Endometrioid) and normal ovary tissues (N) that are either in whole mount sections or tissue arrays were analyzed with IHC. DAB staining was visualized by brightfield microscopy. (C) Detection of protein levels of KLK6 and KLK7 in serous carcinomas by immunohistochemistry, observed under 40× magnification in order to visualize the nuclear stain.

Transcripts of KLK6 and KLK7 were expressed at a basal level in normal ovaries. The expression of these two genes increased significantly in tumors versus controls, and their expression was limited exclusively to the epithelium compartment of all ovarian tumors analyzed (FIG. 4A). In all cases analyzed, neighboring tumor stroma, regardless of subtype, was negative for expression. Moderate differences in staining intensities were observed between low versus high grade, and early versus late stages, of the ovarian tumors (data not shown).

Immunohistochemical analysis of KLK6 and KLK7 on the same set of tissues demonstrated that protein expression patterns of KLK6 and KLK7 were identical to those seen by in situ hybridization (FIG. 4B). Both proteins were expressed exclusively in tumor epithelium of serous, endometroid and papillary serous cancers, whereas the neighboring stroma is minimally positive in all subtypes of ovarian tumors tested (FIG. 4B). Location of KLK7 protein is predominantly cytoplasmic in ovarian cancer cells, whereas that of KLK6 is both cytoplasmic and nuclear (FIG. 4C).

Immunohistologic analysis of normal ovarian tissues demonstrated that KLK6 and KLK7 proteins were exclusively located in the epithelium surface of normal ovarian tissues but not in the neighboring stroma. These results demonstrated that the increase in KLK6 and KLK7 mRNA and protein expression was directly associated with an expansion of tumor cells in the tumor epithelial compartment.

Without being bound by theory, the increase in KLK6 and KLK7 mRNA and protein expression may be related to the secretion of cytokines, growth factors, steroids and the expression of hormone receptors on the ovarian surface epithelium in epithelial ovarian cancers. It is understood that kallikreins are more enzymatically active and expressed at higher levels around the ovulation period when the ovaries are stimulated by gonadotrophin (Holland A M, Findlay J K, Clements J A. Kallikrein gene expression in the gonadotrophin-stimulated rat ovary. J Endocrinol 2001; 170:243-50). As such, steroid hormone-related signaling has also been found in other cancer types (Graham J D, Mote P A, Salagame U, Balleine R L, Huschtscha L I, Clarke C L. Hormone-responsive model of primary human breast epithelium. J Mammary Gland Biol Neoplasia 2009; 14:367-79; Langner C, Ratschek M, Rehak P, Schips L, Zigeuner R.

Steroid hormone receptor expression in renal cell carcinoma: an immunohistochemical analysis of 182 tumors. J Urol 2004; 171:611-4; Kumar R, Gururaj A E, Vadlamudi R K, Rayala S K. The clinical relevance of steroid hormone receptor corepressors. Clin Cancer Res 2005; 11:2822-31). The up-regulation of KLK6 and KLK7 in ovarian cancer thus may involve additional co-factors or unique properties of hormonal surge.

Example 6: Levels of KLK6 and KLK7 mRNA are Elevated in Biopsy Samples from Early Stage Papillary Serous and Serous Ovarian Cancer Patients In this study, elevated expression of KLK6 and KLK7 at early stages of serous and papillary serous ovarian carcinomas, which comprise the most frequently diagnosed ovarian tumors, was found from analysis of a total of 59 early stage ovarian cancer samples obtained from Thomas Jefferson University and MD Anderson Cancer Center tissue archives.

Figure 5:
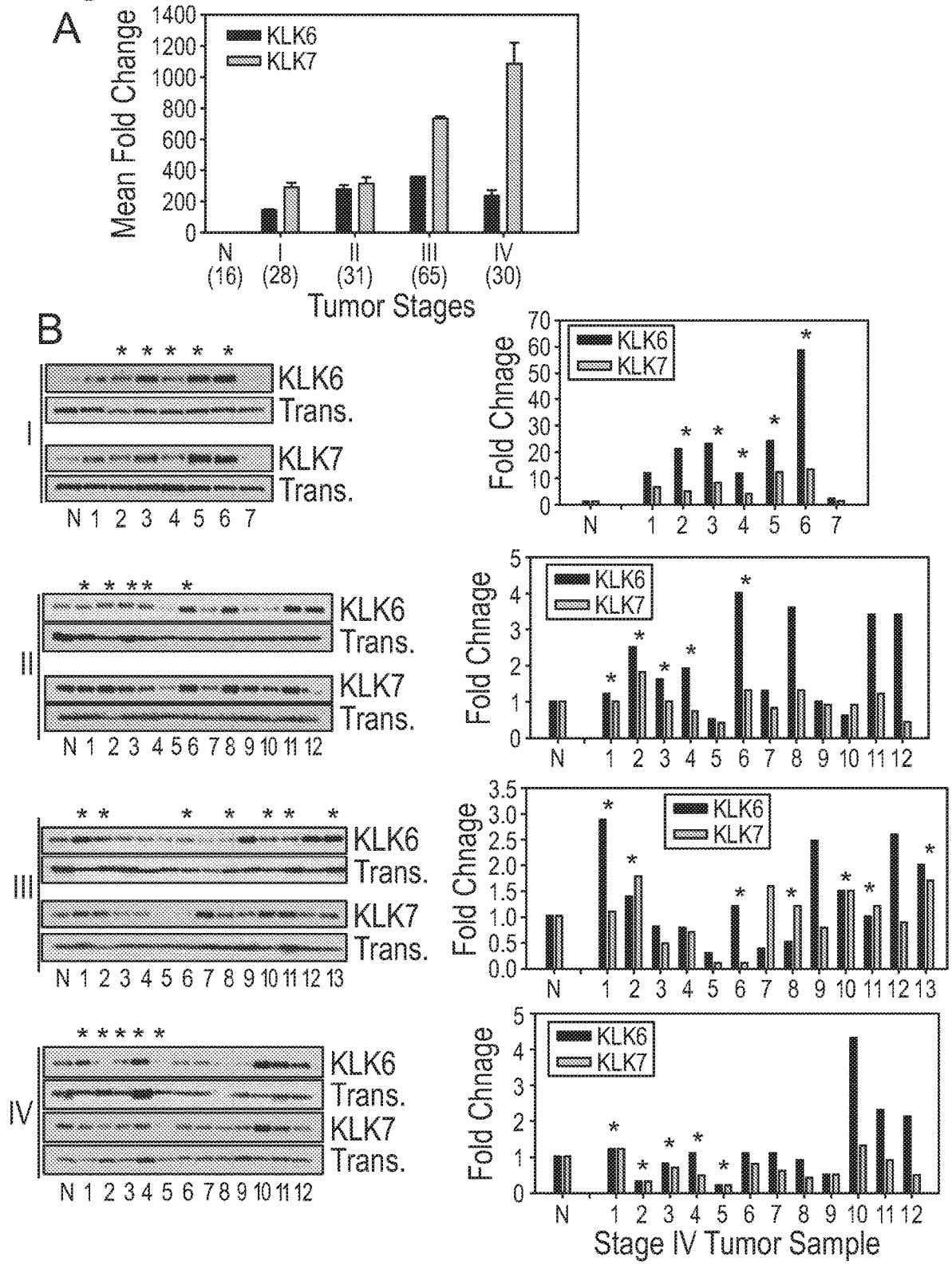
FIG. 5 shows levels of KLK6 and KLK7 proteins in serum samples from early stage serous carcinomas and in human ovarian cancer cell lines. (A) Gene expression of KLK6 (solid black bar) and KLK7 (solid gray bar) in serous and papillary serous carcinomas from each tumor stage (I, II, III, and IV) was analyzed by qRT-PCR, and the mean fold changes were calculated by normalizing against expression in normal epithelial ovary tissues (N). The numbers of samples used in the analyses are denoted in parentheses, and standard error bars are indicated. (B) Specific protein expression analyzed in immunoblots of pooled normal (N) donor sera (n=11) and various subtypes of ovarian cancer patients from multiple stages (I, II, III, and IV). Albumin and IgG were depleted from the serum samples using ProteoPrep Blue Albumin and IgG depletion kit (Sigma-Aldrich) prior to electrophoresis (SDS-PAGE). Expression of KLK protein in each sample was normalized versus the internal transferrin signal. The histograms in graphs adjacent to the immunoblots display the fold changes in KLK protein expression levels, normalized against pooled normal (N) serum and transferrin, as measured by quantitative densitometry. An asterisk (*) indicates serous and papillary serous carcinomas.

KLK6 and KLK7 mRNA expression was elevated in all tumor stages of serous and papillary serous carcinomas versus normal ovarian epithelial tissues (FIG. 5A). Transcripts were overexpressed from nearly 200-fold to over 300-fold in stage I or II carcinomas versus normal ovary tissues (p<0.001 for both KLK6 and KLK7), indicating their utility as biomarkers for early detection of serous and papillary serous subtypes in biopsy samples. In these subtypes of ovarian tumors, the expression of KLK7, but not KLK6, continues to increase in stage III and stage IV.

Example 7: Levels of KLK6 and KLK7 Proteins are Elevated in Sera from Early Stage Papillary Serous and Serous Ovarian Cancer Patients KLK family members are secreted proteins (Henkhaus R S, Roy U K, Cavallo-Medved D, Sloane B F, Gerner E W, Ignatenko N A. Caveolin-1-mediated expression and secretion of kallikrein 6 in colon cancer cells. Neoplasia 2008; 10:140-8). In this study, the protein levels of KLK6 and KLK7 in sera obtained from ovarian cancer patients was further investigated by immunoblot analysis.

Serum samples were pre-cleared to deplete the most abundant serum proteins. KLK6 and KLK7 did not bind to serum proteins that were bound to the pre-clearing column (data not shown). Both KLK6 and KLK7 protein expression was significantly elevated in serum samples from stage I serous and papillary serous ovarian cancer versus pooled normal serum (FIG. 5B). Other subtypes showed mixed expression levels in the serum samples from early stage tumors. The mean fold increase in serous and two subtypes in stage I versus pooled normal serum was determined by densitometry to be 22-fold for KLK6 and 6.7-fold for KLK7 (p<0.01, FIG. 5B), suggesting that both KLK6 and KLK7 can be used as early detection biomarkers in serum samples.

As opposed to KLK6 and KLK7 levels in ovarian cancer tissue, KLK6 and KLK7 levels in serum, when measured by immunoblotting, reach a peak at stage I and then decrease in stages III and IV. The mechanisms underlying the decreased KLK6 and KLK7 protein levels detected in stage III and stage IV ovarian cancer are not understood. Without being bound by theory, possible explanations include blockade of secretion pathways or loss of epitopes by enhanced proteolysis of KLK6 and KLK7.

Example 8: KLK6 and KLK7 can Complement Established Ovarian Cancer Biomarkers HE4 and CA125 for Early Detection of Ovarian Cancer The most common measurements that clinicians use to detect ovarian cancer are of CA125 levels, in addition to pelvic examination, ascites and consideration of family history. Due to the limitations of CA125 for early detection of ovarian cancer, the addition of HE4 (considered to be an early detection biomarker) to CA125 may improve overall sensitivity but may not be sufficient for detecting different subtypes of ovarian cancer. In this study, ELISA assays were used to detect CA125 and HE4 in early stage ovarian cancer patients.

Figure 6:
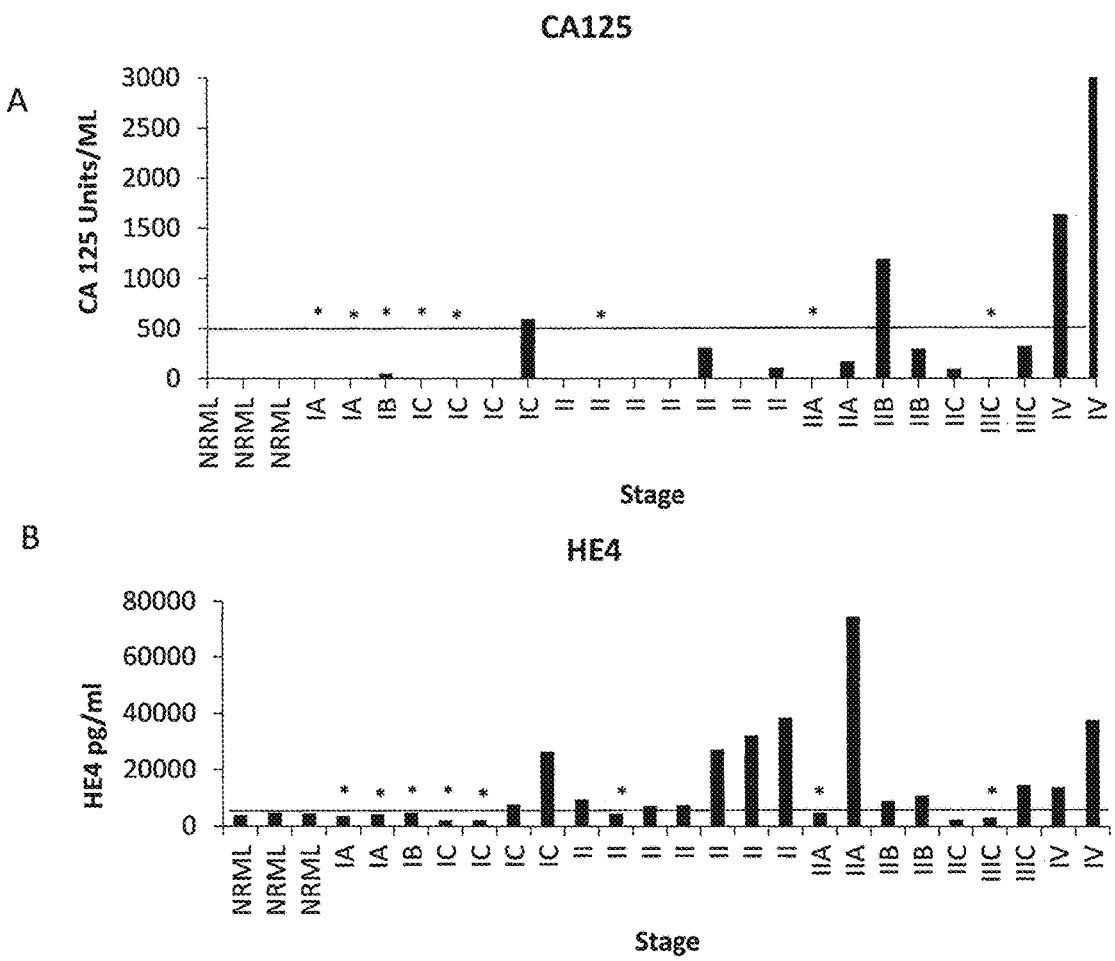
FIG. 6 shows CA125 and HE4 ELISA results for serum samples of early stage serous carcinoma patients. (A) Production of CA125 protein as measured by ELISA. (B) Production of HE4 protein as measured by ELISA. CA125 and HE4 protein levels were calculated as averages of triplicates. The line across the bottom of (A) and (B) indicate the low threshold for CA125 (A) or HE4 (B) upregulation. An asterisk (*) indicates that a particular patient demonstrated no upregulation of both CA125 and HE4. NRML=normal ovarian control.

ELISA assays to detect CA125 and HE4 in early stage ovarian cancer patients demonstrated that CA125 was detected above normal levels in only 7 out of 19 early stage patients; and in 3 out of 4 advanced stage (stages IIIC and IV) patients (FIG. 6). Highest levels of CA125 and HE4 overall were measured in stage IV patients. HE4 was found in 11 out of 19 early stage patients and in 3 out of 4 advanced stage patients. Highest levels were detected in one stage IIA patient, in three stage II patients, as well as in one stage IV patient. These results indicate that sensitivity (or true positive rate) was only 0.61 for CA125 and 0.7 for HE4 in early stage patients (Stages I and II) suggesting that CA125 and HE4 do not sufficiently complement each other for use as early detection ovarian cancer biomarkers.

Based on the results, a group of seven (7) "false-negative" patients was defined for both CA125 and HE4. This group included four (4) patients in stage I, two (2) patients in stage II and one (1) patient in stage III. When the same patient population was analyzed for expression of KLK6 and KLK7 by immunoblotting, as demonstrated in FIG. 5B, both proteins were significantly upregulated, particularly in Stage I serous and papillary serous ovarian carcinoma.

Figure 7:
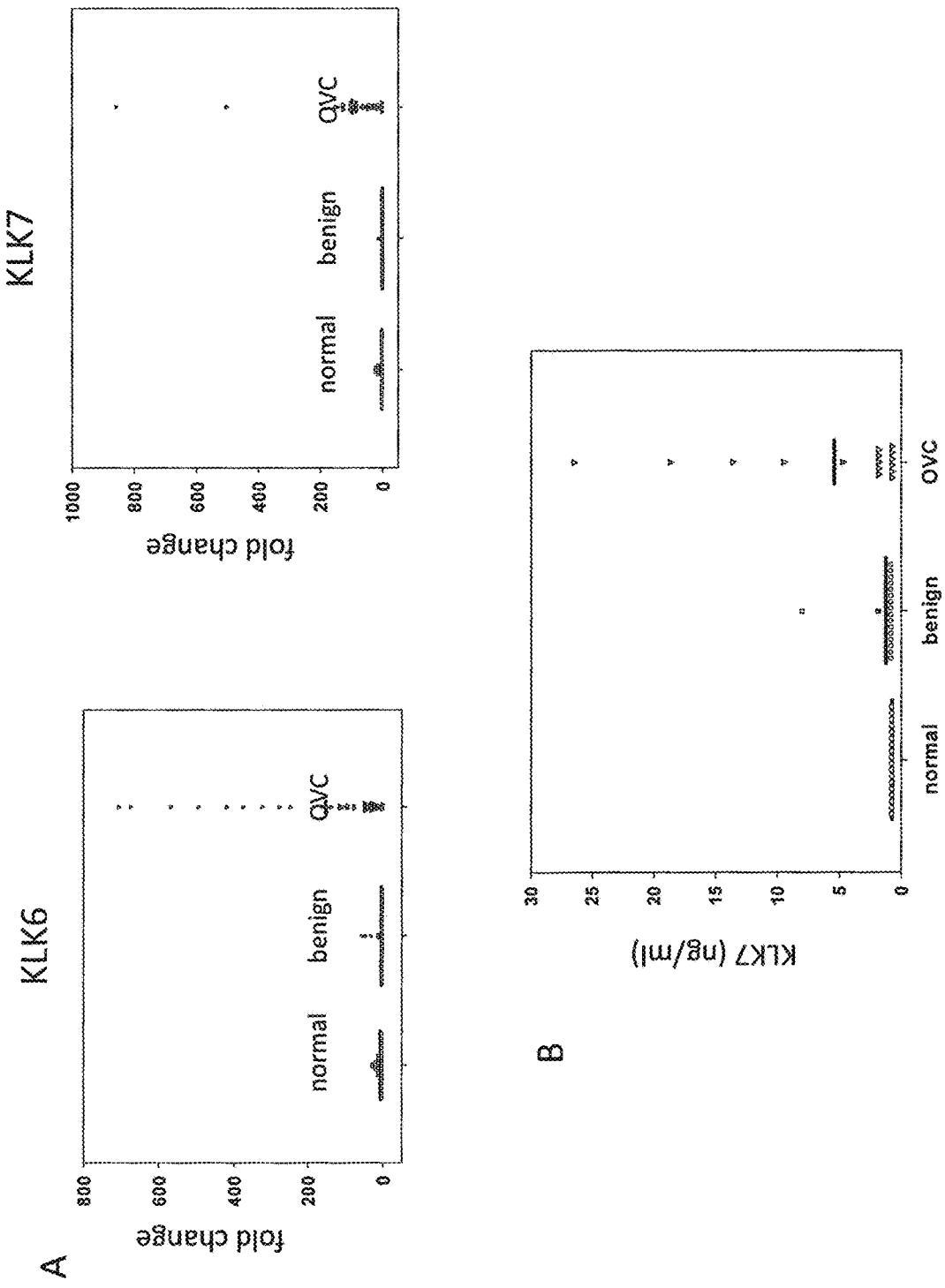
FIG. 7 shows KLK6 and KLK7 protein expression in samples obtained from normal, benign and ovarian cancer (OVC) individuals. (A) KLK6 and KLK7 staining was measured in OVC (n=38), benign (n=44) and normal individuals (n=42) by immunohistochemistry (IHC). In KLK6, benign levels were significantly lower compared to normal and OVC ($P<0.05$). In KLK7, OVC levels were significantly higher compared to the benign group ($p<0.05$). (B) Serum levels of KLK7 were measured in cancer (n=17), benign and normal (n=19 in each group). $P<0.05$ between normal and OVC groups. Horizontal lines indicate mean values.

The preliminary serum ELISA data indicated that levels of KLK7 protein in ovarian cancer patients were significantly higher compared to KLK7 protein levels in normal individuals (p<0.05). There was no significant difference in serum KLK7 protein levels between benign and normal individuals (P>0.05) (FIG. 7). Similarly, Shan et al. reported that tissue KLK6 concentrations were significantly elevated in ovarian cancer group (N=259) compared to its levels in benign (N=49) and normal (N=34) groups (P<0.001). No significant difference in KLK6 concentrations were detected between the benign and the normal group (Shan S J et al., Transcriptional upregulation of human tissue kallikrein 6 in ovarian cancer: clinical and mechanistic aspects. Br. J. Cancer, 2007. 96(2): p. 362-72).

Example 9: Over-expression of PRSS8 is Highly Specific to Ovarian Cancer

In this study, PCR, in situ hybridization and immunohistochemical analysis was used to determine expression of PRSS8 on tissue of noimal ovary, ovarian cancer and other cancer types, as well as on normal and ovarian cancer cell lines.

Figure 8:
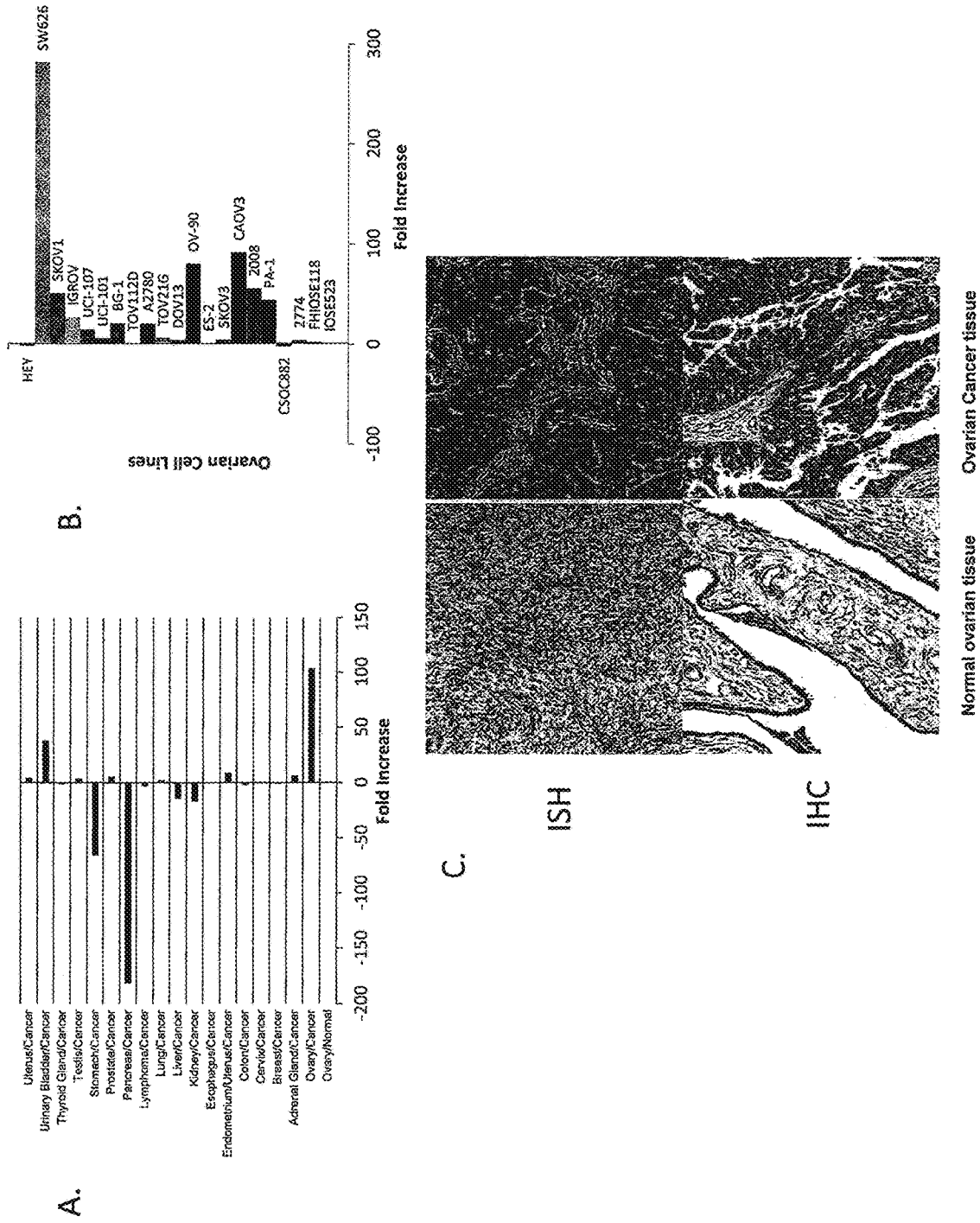
FIG. 8 shows expression of PRSS8 on tissue of normal ovary, ovarian cancer and other types of cancer (A), on normal and ovarian cancer cell lines (B) and as detected by in situ hybridization (ISH) (C—top) and immunohistochemistry (IHC) (C—bottom) in normal and ovarian cancer tissues (magnification of ×20). In panel A, over 390 cDNAs derived from 19 different cancer tissues and corresponding normal tissues were assayed by RT-qPCR to quantitatively measure PRSS8 gene expression. The fold change represents the level of gene expression in cancer normalized against the corresponding normal tissue. The mean number of samples used in the assay was 18 for cancer and 1 for normal tissue. In panel B, gene expression of PRSS8 in ovarian cancer cell lines (solid black bars) and normal ovary cell lines (N) was analyzed by qRT-PCR and normalized against a "primary-like" normal ovarian cell line IOSE523. IOSE523 begins to senesce after twenty passages while FIOSE118 is immortal. The mean fold change represents triplicate measurements. In panel C, top section, mRNA from tissues of ovarian tumors in normal individuals and ovarian cancer patients were hybridized in situ with PRSS8 oligo-nucleotide probes followed by visualization of red chromogen staining by bright-field microscopy under 20× magnifications. In panel C, bottom section, to detect PRSS8 protein expression in normal and cancer patients, tissues that were either in whole mount section or tissue arrays were analyzed with IHC. 3,3′-Diaminobenzidine (DAB) staining was visualized by bright-field microscopy. Detection of protein levels of PRSS8 by immunohistochemistry was observed under 20× magnifications in order to visualize the nuclear stain.

All of the selected 13 genes (Example 1) were subjected to a final screening step by using normal and cancer samples that represent 18 tumor types and over 390 individuals (Tissue Scan from Origene, data not shown). From this screening step, PRSS8 gene was chosen based on the specificity and the level of up-regulation in ovarian cancer when compared with other cancer types. The differential gene expression of PRSS8 between ovarian cancer and normal ovarian tissues was over 100 fold (FIG. 8A). Among the non-ovarian cancers tested, urinary bladder cancer was the only cancer over-expressing PRSS8, although to a much lesser degree compared to ovarian cancer (FIG. 8A). PRSS8 is down-regulated on tumor cells of pancreatic cancer (X180) and, to a lesser extent, on those of stomach cancer (FIG. 8A).

FIG. 8B shows PCR analysis of PRSS8 expression on 2 normal and 18 ovarian cancer cell lines. PCR analysis revealed that 10 of the 18 ovarian cancer cell lines tested over-expressed PRSS8 protein (i.e., prostasin), while the PRSS8 protein was negatively expressed on normal cell lines (FHIOSE118 and IOSE523). The cancer cell lines SW626 and CAOV3 demonstrated increased expression of PRSS8 nearly 300 fold and 100 fold, respectively (FIG. 8B).

In order to observe the level of both PRSS8 gene and PRSS8 protein expression, staining of PRSS8 in ovarian cancer tissue as compared to normal ovarian tissue was performed, using in situ hybridization and immunohistochemistry. For the former technique, a customized probe was hybridized in situ with over 500 normal and ovarian tumor tissues in a tissue array format. PRSS8 transcript was expressed at a basal level in normal ovaries, but the expression level of the gene increased significantly in the epithelium compartment of tumors (FIG. 8C, top panels). In all cases, neighboring tumor stroma compartment was not stained. Without being bound by theory, this data suggests exclusive expression of PRSS8 in the tumor epithelia. The difference in gene expression for PRSS8 between mucinous versus serous and borderline subtypes was consistent at the tissue level. The immunohistochemical staining of PRSS8 proteins was identical to the in situ staining pattern (FIG. 8C, bottom panels). The PRSS8 protein stained positive for cytoplasm of tumor epithelia, while the staining was absent in the nucleus. Without being limited by theory, this data suggests that gene over-expression translates to high level of protein production. The neighboring stroma that is adjacent to tumor epithelia were minimally stained for both proteases. This signature of basal level staining coincided with the in situ data.

These data indicate that PRSS8 is specific to ovarian cancer tissues and is expressed on many ovarian cancer cell lines as compared to normal tissues and cells.

Example 10: PRSS8 is Over-expressed on Tissues from Patients with Early Stages/Grades of Ovarian Cancer and Remains Over-expressed Throughout the Stages of the Disease Since our goal was to explore the potential of PRSS8 as an early detection biomarker for ovarian cancer, this study measured the expression of PRSS8 protein in different stages of malignancy.

Ovarian cancer (OVC) stage indicates how far the tumors have spread beyond the ovaries and is determined by procedures such as biopsies and cytological analyses. Briefly, in stage I OVC, the tumor is confined to one or both ovaries. In stage II, the tumor is localized within the pelvic organs such as uterus and fallopian tubes and has not yet spread to the abdominal organs. Stage III indicates that the tumor has reached abdominal organs or the lymphatic system. In stage IV, the tumor has reached distal organs such as lung, liver, brain etc. Each stage can be further divided into three categories (A, B and C). In this study, patient data was grouped into 7 stage categories: Stage I-IA (n=25), IB-IC (n=18), IIA-B-C(n=18), III-IIIA (n=19), IIIB (n=23), IIIC (n=45) and IV (n=11).

Figure 9:
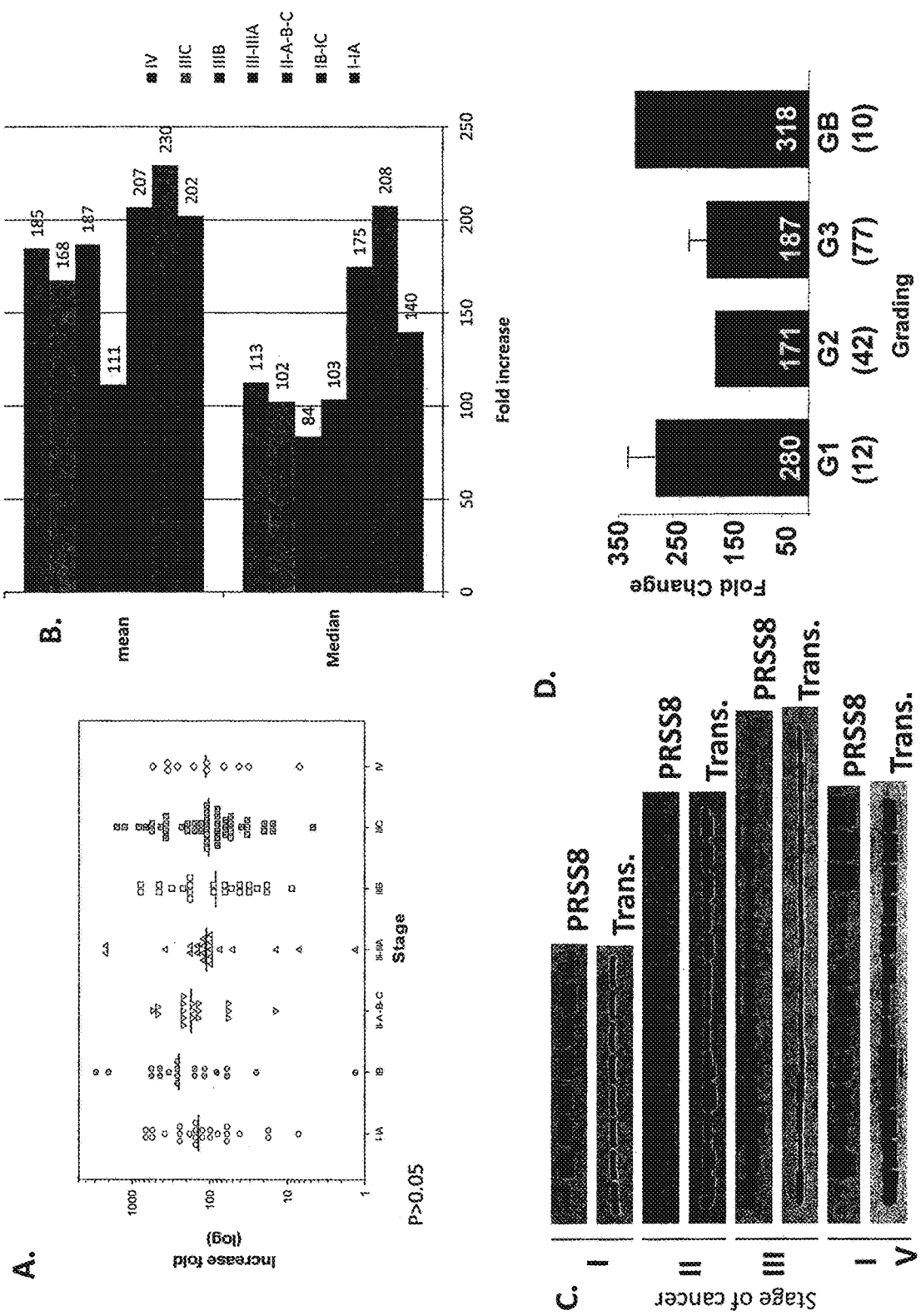
FIG. 9 shows PRSS8 expression in early-stage ovarian cancer (OVC). PRSS8 gene expression levels were measured in tumor tissues of ovarian cancer patients in different stages of the disease and were plotted as individual fold increase (A) and by average and mean (B). Variable number of serum samples, stage I (8 samples), II (13), III (15), 4 (13) were stained and analyzed by western blotting (C). Average levels of PRSS8 in tumor tissues of ovarian cancer patients are presented as a function of different grades of the disease (D).

RT-PCR analysis of patients' tumor cells was conducted and expression of PRSS8 (as fold increase over expression in normal individuals) is shown in FIG. 9. FIG. 9A shows individual PCR results as a function of patients in different groups of cancer stage (stage I to stage IV). Due to differences in the number of patients (n) in each group, unpaired t-test was performed. No significant differences between the groups of patients in different stages was observed (P>0.05). However, nearly all patients exhibited increased levels of PRSS8 as compared to normal individuals. FIG. 9B shows the median and the mean of PRSS8 expression within and between different cancer stages/groups of patients. The bar graph demonstrates that PRSS8 can be used as a marker for early detection of ovarian cancer, as these measures were notably higher in the early stage groups (e.g., stages I and II).

Western Blot staining of individual sera from OVC patients in various stages of the disease corresponded to the data obtained from RT-PCR analysis of OVC patient tissues. FIG. 9C shows that PRSS8 protein expression was observed in the majority of stage I and II patient sera. Similar to the PCR data, weaker expression was observed in stage III and IV patients although all bands were visible. These expression-by-stage results indicate that PRSS8 is expressed throughout the stages of OVC, with higher expression observed in the early stages (e.g., stages I and II).

Ovarian cancer (OVC) is distinguished not only by stages but also by grades. While OVC stage indicates how far the tumor has metastasized, OVC grade indicates the abnormality of the tumor cells (as observed through a microscope). That is, OVC grade is indicative of the aggressiveness of the tumor cells. Briefly, ovarian cancers are graded from grade 1 to grade 3: grade 1 indicates that the cells appear close to normal and grade 3 is defined by very abnormal-looking cells (i.e., highly aggressive). Grade 2 is assigned to OVC cells that are observed to be between the grade 1 and grade 3. In addition, grade GB indicates a boarder-line tumor that is an epithelial type of OVC with a low malignancy potential.

FIG. 9D shows that PRSS8 expression is up-regulated in patients of all OVC grades. Scores were particularly high in grades I and in GB. These results indicate that PRSS8 can be used as a biomarker for detection of early stage/grade ovarian cancer. It should be noted that the number of patients in each group significantly varies, pertaining to the nature of this malignancy. Ovarian cancer is normally detected in the late stages of the disease, thus resulting in a high mortality rate for OVC patients.

In a separate analysis, it was determined whether the level of PRSS8 gene expression increased with age of patients across the various stages of OVC. No correlation between PRSS8 gene expression levels across all stages, within each stage or between ages was identified (data not shown). This analysis indicates that PRSS8 can be used for early detection of OVC regardless of the patient's age.

Example 11: PRSS8 is Over-Expressed in all Main Subtypes of Ovarian Cancer (OVC) and Demonstrates Significant Over-Expression in Serous OVC Patient Tissue It is thought that most ovarian cancer subtypes, such as serous, papillary-serous, mucinous, clear cell and endometrioid, have a different history of initiation and development. However, most OVC biomarker studies and treatment protocols are not subtype-specific.

In this study, levels of PRSS8 were measured in patients with different subtypes of OVC.

The results of this study indicate that PRSS8 expression level in serous patients is significantly higher (P<0.05) compared to papillary-serous patients. Expression of PRSS8 was not significantly different in endometrioid patients as compared to any of the above groups. Due to the lower number of patients in the clear cell and borderline patients (8 and 11 patients, respectively), results in these groups were presented but not statistically analyzed.

Figure 10:
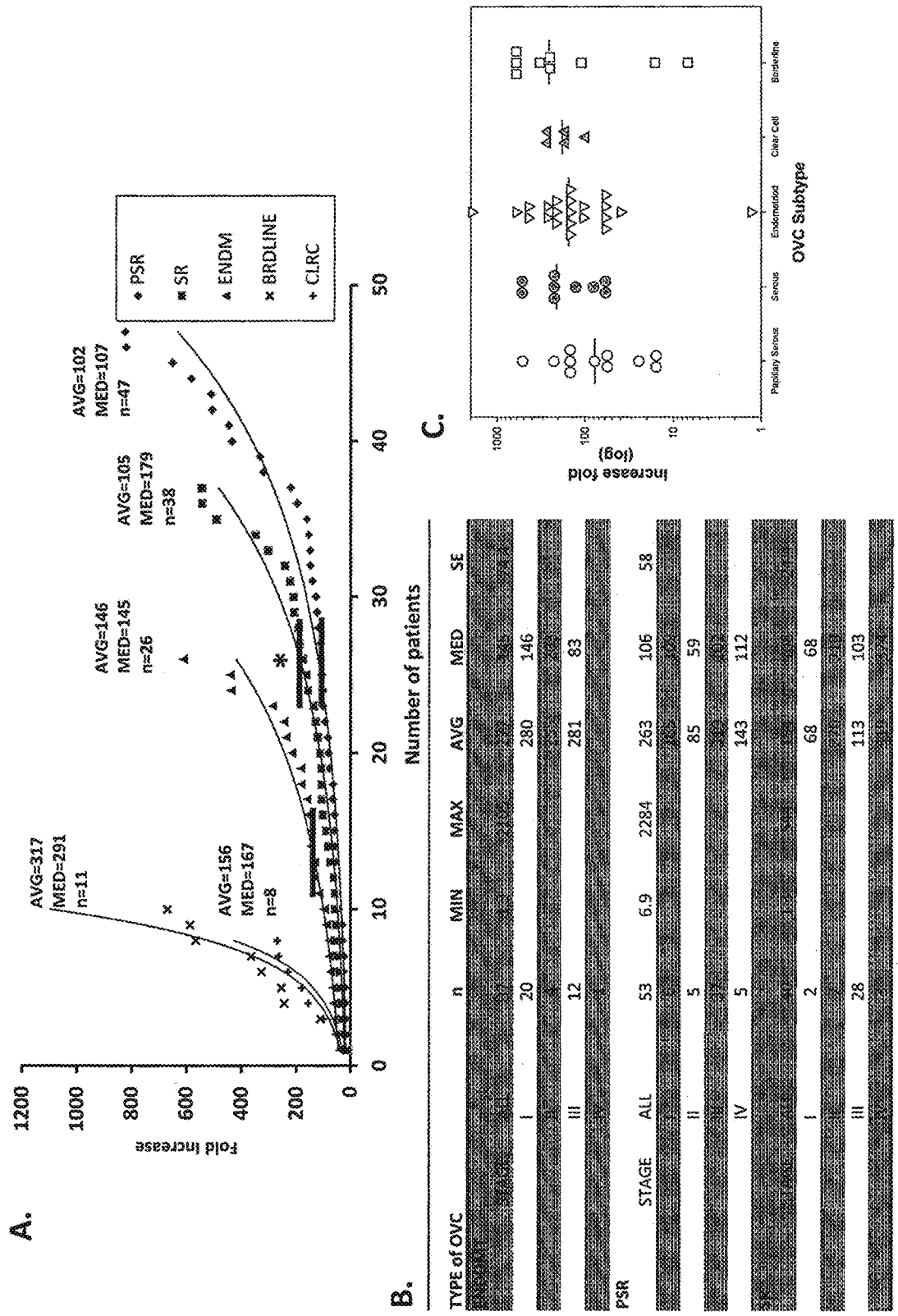
FIG. 10 shows PRSS8 expression in ovarian cancer (OVC) classified in different groups. (A), thick black lines represent median level of expression in each group. (*) represents significant difference ($p<0.05$). PSR=papillary serous; SR=serous; ENDM=endometrioid; BRDLINE=borderline; CLCR=clear cell. Detailed analysis of the expression levels in each group is provided in tabular form (B). Expression of PRSS8 in early stage patients (stages I and II) is presented within groups of 5 different OVC subtypes (C). Results are presented as fold increase over expression in normal individuals.

Expression of PRSS8 in patients with different types of OVC by stage of the disease was further analyzed (FIG. 10B). Notably, levels of PRSS8 protein were up-regulated in all types of stage II OVC and remained up-regulated throughout the stages. Due to the high standard deviation between the patients in each group, median values were lower than average values and further statistical analysis was not possible due to the low number of patients in each category. In endometrioid OVC type, more than 50% of the patients (20/37) were detected in stage I, while in serous and papillary serous OVC, the majority of the patients were detected in stage III (28/40 and 37/53, respectively). Without being bound by theory, this may be due to the different nature of metastasis of these OVC subtypes. While endometrioid and clear cell tend to stay confined to the ovaries, serous and papillary serous subtypes aggressively metastasize to other organs. Because serous and papillary serous subtypes present no early specific symptoms, they are often detected at a later stage.

These data indicate that KLK6, KLK7 and PRSS8 are selective biomarkers for early detection of the most common types of ovarian cancer and may complement CA125 and HE4 as early detection tumor biomarkers.

Example 12: Localization of PRSS8 Protein in Ovarian Tissues of OVC, Benign and Normal Individuals and in Non-OVC Cancer Tissues Tissue arrays of OVC, benign and normal cases were stained for PRSS8 by immunohistochemistry (magnification 40×). Tissue arrays were generated from normal ovary (A1), serous adenocarcinoma with control (A2), endometriod adenocarcinoma with control (A3), serous cystadenoma with control (A4), benign ovary tissue (B1), serous adenocarcinoma various tissue arrays (C1), papillary serous adenocarcinoma various tissue arrays (C2), mucinous adenocarcinoma various arransy (C3), endometriod adenocarcinoma (C4), clear cell various arrays (C5), borderline carcinoma (C6), transitional cell carcinoma (C7), cancer (non-OVC) (D1 and D2).

Immunostaining of all tissue arrays used in this study were given scores (0-3) according to levels of staining, where a score of (0) means negative staining, (1) means weak positive staining, (2) means positive staining, and (3) means strong positive staining. Bar plots of PRSS8 immunostaining score by OVC stage (E1) and by OVA grade (E2). n=number of stained arrays in each group.

Figure 12:
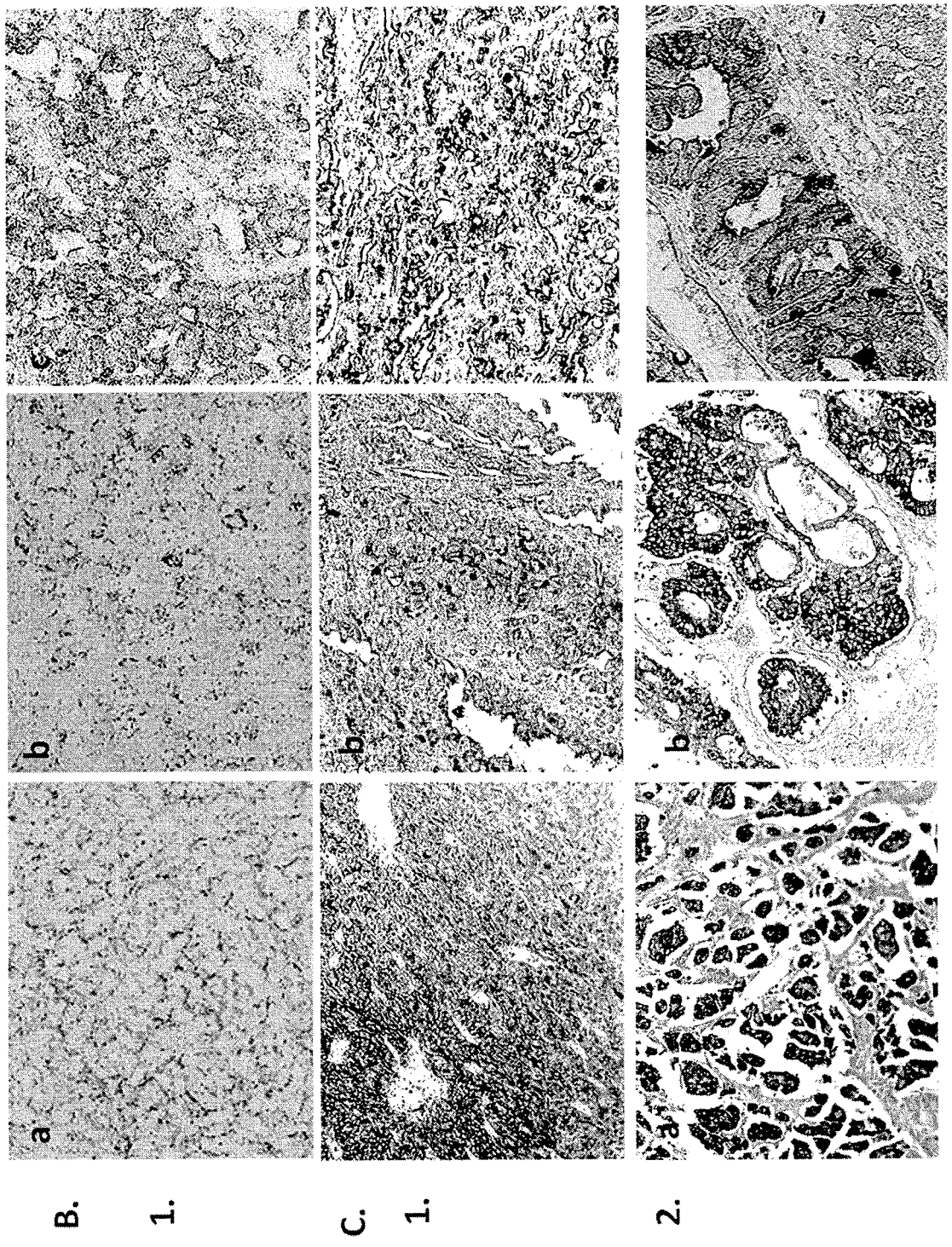
FIG. 12 shows tissue arrays of OVC, benign and normal cases stained for PRSS8 by immunochemistry (magnification 40×).
Figure 12:
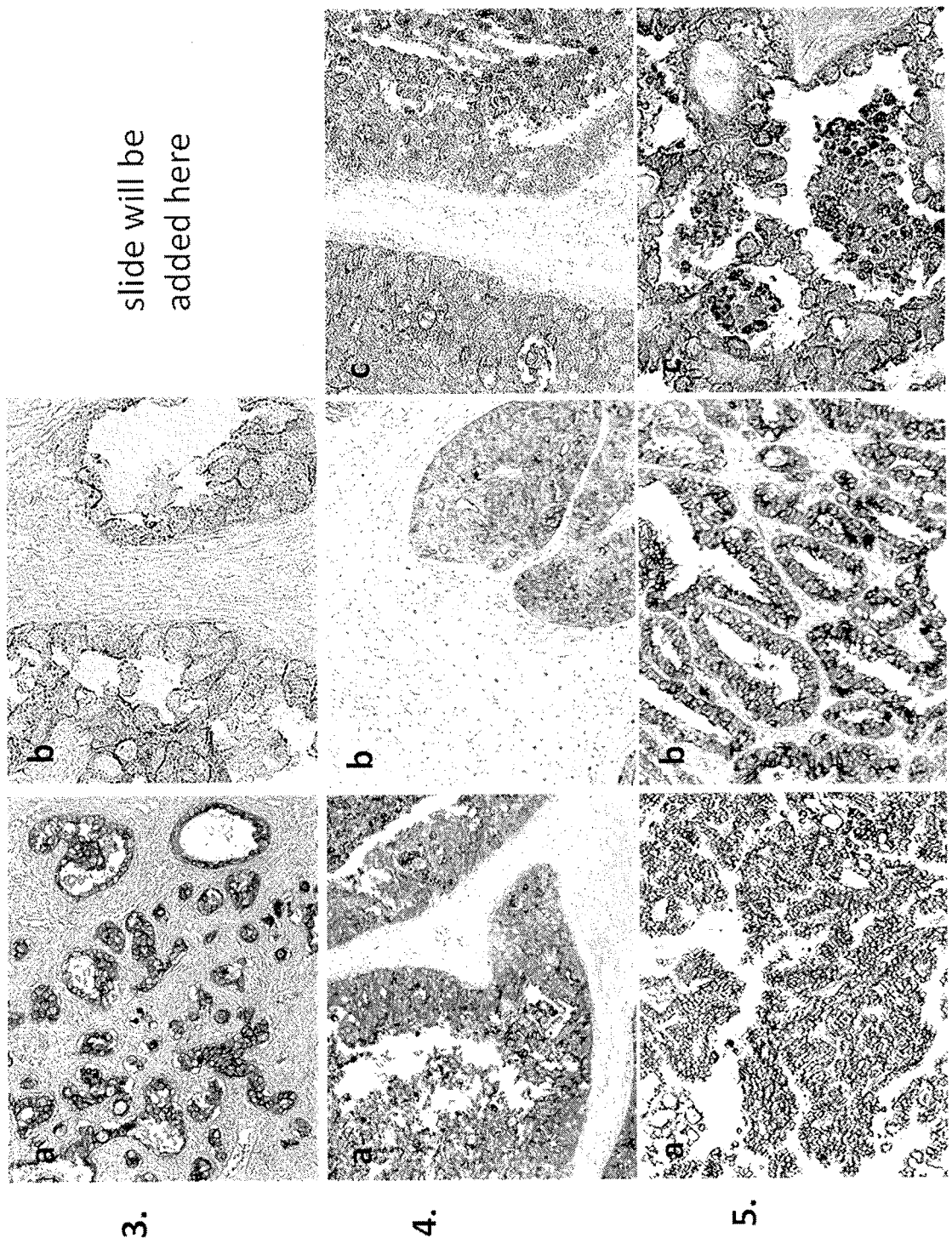
Figure 12:
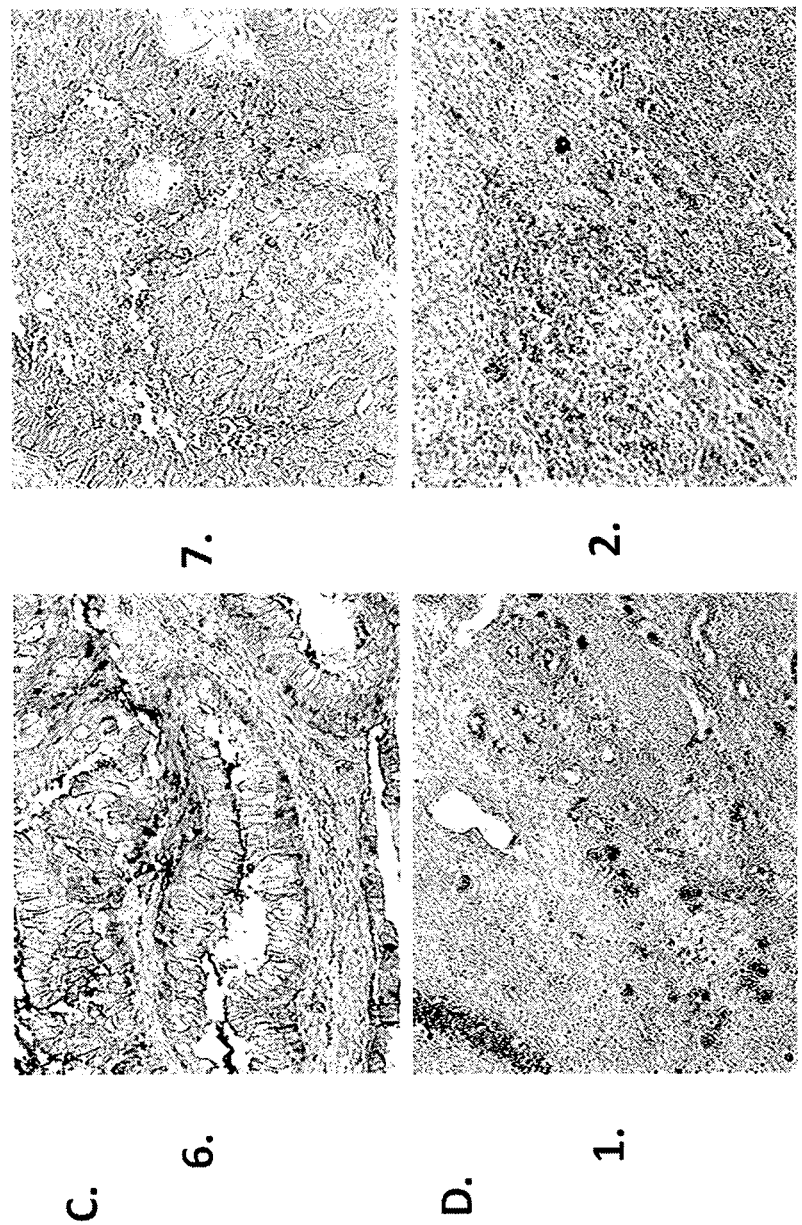
Figure 12:
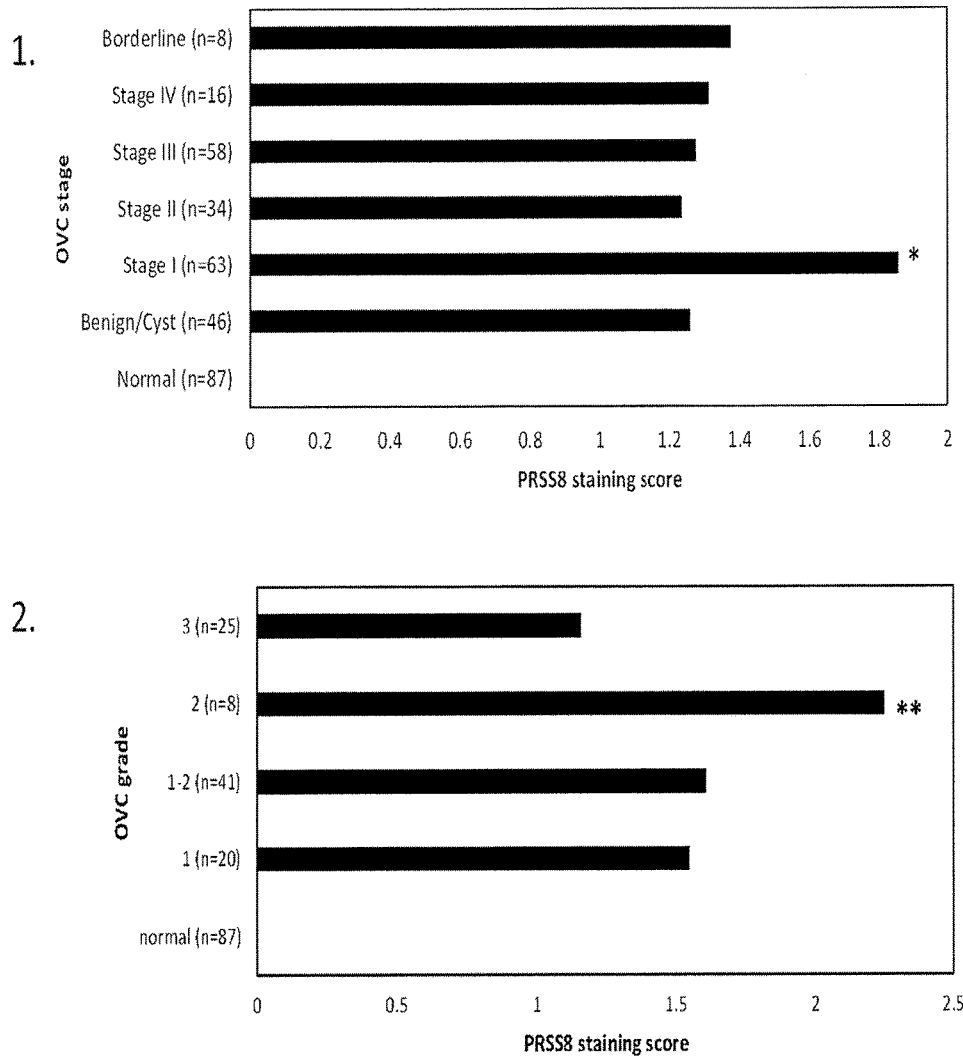

PRSS8 does not appear in ovary tissue sections of normal individuals (FIG. 12A1b) compared to the same sections stained with a negative control (FIG. 12A1a). PRSS8 was abundant in tissue sections derived from OVC patients in early stage (FIGS. 12A2b and 12A3b) as well as in late stage (FIG. 12A4b) as compared to their corresponding negative control staining (FIG. 12A2a, A3a and A4a, respectively). Next tissue sections of several cases of benign conditions such as theca call tumors and chocolate and simple cysts (n=46 overall)) were stained. It was found that PRSS8 appears in tissues derived from benign patients, who had theca cell tumors (FIGS. 12B1a and 12B1b) and chocolate cyst (FIG. 12B1c), although patterns of staining were noticeably different compared to those observed in OVC patients. Tissue sections of different subtypes of OVC patients in early stages of the malignancy (FIG. 12C) were stained and presented three cases for each subtype (a, b and c). Although the staining patterns were sometimes different among the different OVC subtypes, it is noticeable that PRSS8 is upregulated in these tissues from an early stage of the disease. Sections were generated from serous (FIG. 12C1), papillary serous (FIG. 12C2), mucinous (FIG. 12C3), endometriod (FIG. 12C4) and clear cell (FIG. 12C5) carcinoma. Representative staining of tissue sections derived from borderline (FIG. 12C6) and transitional (FIG. 12C7) OVC also are shown. In addition, when tissue sections were generated from adjacent cancerous tissues (non-OVC) such as in cancer of the omentum (FIG. 12D1) and mixed mullerian tumors (FIG. 12D2), nearly no PRSS8 staining was observed. Finally, dot plots of scoring tissue sections derived from normal, benign, and OVC by PRSS8 staining across different stages and grades were presented. FIG. 12E1 shows that PRSS8 was present in tissue sections derived from OVC patients as well as from benign condition patients (theca tumors and cysts) but not in ovarian tissues of normal individuals. Staining patterns of OVC tissues were different as compared to those derived from benign patients. PRSS8 protein was significantly more abundant in tissues derived from Stage 1 OVC patients compared to patients in other stages and in benign conditions (P<0.01). When similar analysis was performed by OVC grade, tissue sections from grade 2 patients contained more PRSS8 as compared to other OVC grades (P<0.05). These results indicate that PRSS8 is upregulated in OVC tissues from early stage disease and is not present in ovary tissue of normal individuals. The immunohistochemistry staining also showed that PRSS8 is present in tissue sections derived from patients with benign conditions.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating early stage (I/II) ovarian cancer in an subject comprising:
   (i) detecting the presence of early stage (I/II) ovarian cancer in the subject by:
   (a) obtaining a serum sample from the subject and obtaining a normal serum control sample;
   (b) isolating from the sample obtained in (a) total RNA comprising mRNA encoding the serine protease prostassin (PRSS8) and at least one additional serine protease selected from kallikrein 6 (KLK6) or kallikrein 7 (KLK7);
   (c) transforming the isolated total RNA of (b) into cDNA comprising serine protease cDNA;
   (d) amplifying the cDNA of (c);
   (e) measuring a level of amplified serine protease cDNA in (d) as a measure of expression of amplified serine protease mRNA;
   (f) comparing the level of expression of the amplified serine protease mRNA in (e) expressed by the subject with the level of expression of the amplified serine protease mRNA in (e) expressed by the normal serum control sample, wherein an increased level of expression of the serine protease mRNA expressed by the subject compared to the level of expression of the serine protease mRNA expressed by the normal serum control sample is indicative of early stage ovarian cancer in the subject;
   (ii) when (f) is indicative of detecting early stage (I/II) ovarian cancer in the subject, identifying an increased level of expression of serine protease mRNA expressed by the subject compared to the level of expression of the serine protease mRNA expressed by normal ovarian tissue control sample by:
   (g) obtaining an ovarian tissue sample from subject;
   (h) isolating from the ovarian tissue sample obtained in (g) total RNA comprising serine protease mRNA;
   (i) transforming the isolated total RNA of (h) into cDNA comprising serine protease cDNA;
   (j) amplifying the cDNA of (i);
   (k) measuring a level of amplified serine protease cDNA in (j) as a measure of expression of amplified serine protease mRNA;
   (l) comparing the level of expression of the amplified serine protease mRNA in (k) expressed by the subject with the level of expression of the amplified serine protease mRNA in (k) expressed by a normal ovarian tissue control sample, wherein an increased level of expression of serine protease mRNA expressed by the subject compared to the level of expression of the serine protease mRNA expressed by the normal ovarian tissue control sample is indicative of early stage ovarian cancer in the subject;
   (iii) diagnosing early stage (I/II) ovarian cancer in the subject when both (f) and (I) are indicative of early stage ovarian cancer;
   (iv) identifying the subject diagnosed with early stage (I/II) ovarian cancer as suitable to receive a treatment regimen to treat the early stage (I/II) ovarian cancer; and
   v) effectively treating the subject with a treatment regimen effective to treat the early stage (I/II) ovarian cancer at a stage when the early stage ovarian cancer is responsive to treatment.

2. The method according to claim 1, wherein the ovarian tissue sample is epithelial.

3. The method according to claim 1, wherein the normal serum control sample is a pooled normal serum sample.

4. The method according to claim 1, wherein the amplifying is performed by Reverse Transcriptase-Polymerase Chain Reaction (RT-PCR).

5. The method according to claim 1, wherein the ovarian cancer is selected from the group consisting of serous, papillary serous, metastatic, borderline, mucinous and clear cell.

6. The method according to claim 1, wherein the ovarian cancer is a grade 1 ovarian cancer characterized by:
   (i) well-differentiated tissue; or
   (ii) low grade nuclei with infrequent mitotic figures.

7. The method according to claim 1, wherein the ovarian cancer is a stage I ovarian cancer characterized by:
   (i) a tumor limited to one ovary, capsule intact, no tumor on ovarian surface and negative washings (Stage IA);
   (ii) a tumor involving both ovaries, capsule intact, no tumor on ovarian surface and negative washings (Stage IB);
   (iii) surgical spill (Stage IC1);
   (iv) capsule rupture before surgery or tumor on ovarian surface (Stage IC2); or
   (v) malignant cells in ascites or in peritoneal washings (Stage IC3).

8. The method according to claim 1, wherein the ovarian cancer is a stage II ovarian cancer characterized by:
   (i) extension and/or implant of a tumor on uterus and/or Fallopian tubes (Stage IIA); or
   (ii) extension of a tumor to other pelvic intraperitoneal tissues (Stage IIB).

9. The method according to claim 1, wherein the increased level of expression of the serine protease mRNA expressed by the subject compared to the level of expression of the serine protease mRNA expressed by the normal ovarian tissue control sample is indicative of an expansion of tumor epithelial compartment cells.

\* \* \* \* \*